US006787111B2

(12) United States Patent
Roach et al.

(10) Patent No.: US 6,787,111 B2
(45) Date of Patent: Sep. 7, 2004

(54) APPARATUS AND METHOD FOR FILLING AND CLEANING CHANNELS AND INLET PORTS IN MICROCHIPS USED FOR BIOLOGICAL ANALYSIS

(75) Inventors: David J. Roach, Los Gatos, CA (US); Robert T. Loder, Jr., Sunnyvale, CA (US); Thomas M. Armstrong, Santa Clara, CA (US); Dennis W. Harris, Mt. View, CA (US); Stevan B. Jovanovich, Livermore, CA (US); Richard F. Johnston, Murphys, CA (US)

(73) Assignee: Amersham Biosciences (SV) Corp., Sunnvale, CA (US)

( * ) Notice: Subject to any disclaimer, the term of this patent is extended or adjusted under 35 U.S.C. 154(b) by 549 days.

(21) Appl. No.: 09/737,675

(22) Filed: Dec. 13, 2000

(65) Prior Publication Data

US 2001/0005489 A1 Jun. 28, 2001

Related U.S. Application Data

(60) Continuation-in-part of application No. 09/556,897, filed on Apr. 20, 2000, which is a division of application No. 09/109,676, filed on Jul. 2, 1998.

(51) Int. Cl.[7] ....................... G01N 27/26; G01N 27/403
(52) U.S. Cl. ..................... 422/99; 422/100; 204/601; 204/451; 204/450; 204/600; 134/167 R; 134/167 C; 134/171; 134/166 C; 134/172
(58) Field of Search .................... 422/99–104; 204/601, 204/451, 450, 600

(56) References Cited

U.S. PATENT DOCUMENTS

| 4,554,839 A | 11/1985 | Hewett et al. ........... 73/864.16 |
| 4,635,665 A | * 1/1987 | Namba et al. .......... 134/167 R |
| 4,803,050 A | 2/1989 | Mack ........................ 422/65 |
| 4,909,920 A | 3/1990 | Sarrine et al. .......... 204/299 R |
| 4,938,080 A | 7/1990 | Sarrine et al. ........... 73/864.21 |
| 4,952,518 A | 8/1990 | Johnson et al. ............. 436/518 |
| 5,096,670 A | 3/1992 | Harris et al. .................... 422/65 |
| 5,108,703 A | 4/1992 | Pfost et al. .................... 422/65 |
| 5,274,240 A | 12/1993 | Mathies et al. .......... 250/458.1 |
| 5,376,252 A | 12/1994 | Ekstrom et al. ........ 204/299 R |
| 5,460,709 A | 10/1995 | Sarrine et al. .......... 204/299 R |

(List continued on next page.)

FOREIGN PATENT DOCUMENTS

| JP | 10 148628 | 6/1998 |
| WO | WO00/02038 | 1/2000 |
| WO | WO00/30751 | 6/2000 |
| WO | WO00/52376 | 9/2000 |

*Primary Examiner*—Jill Warden
*Assistant Examiner*—Elizabeth Quan
(74) *Attorney, Agent, or Firm*—Thomas Schneck; David M. Schneck

(57) ABSTRACT

An apparatus for filling and cleaning channels and inlet ports of a microchip substrate is disclosed. A device of the apparatus comprising an array of tubes is inserted into each of the inlet ports of the microchip. The array of tubes of the device comprises a plurality of pressure tubes, surrounded by a plurality of vacuum tubes. In conjunction with this, pressurized solutions such as matrix or wash are introduced into common openings on the microchip that provide a passage to microchannels of the microchip with the use of pressure tip injectors of the apparatus. As matrix or wash solutions are pumped through the common openings and microchannels of the microchip substrate, wash solutions are pumped through the plurality of pressure tubes and everything is vacuumed through the plurality of vacuum tubes surrounding the plurality of pressure tubes. Various reservoirs of solutions are selected and allowed to flow by proper valve actuation. This process can be performed manually or easily automated by utilizing appropriate valves and control hardware/software.

18 Claims, 21 Drawing Sheets

U.S. PATENT DOCUMENTS

| | | | |
|---|---|---|---|
| 5,500,071 A | 3/1996 | Kaltenbach et al. | 156/272.8 |
| 5,571,410 A | 11/1996 | Swedberg et al. | 210/198.2 |
| 5,587,128 A | 12/1996 | Wilding et al. | 422/50 |
| 5,635,050 A | 6/1997 | Pentoney et al. | 204/605 |
| 5,648,266 A * | 7/1997 | Astle | 435/308.1 |
| 5,681,484 A | 10/1997 | Zanzucchi et al. | 216/2 |
| 5,716,825 A | 2/1998 | Hancock et al. | 435/286.5 |
| 5,851,370 A | 12/1998 | Maracas et al. | 204/450 |
| 5,906,723 A | 5/1999 | Mathies et al. | 204/603 |
| 5,916,428 A | 6/1999 | Kane et al. | 204/601 |
| 5,948,359 A * | 9/1999 | Kalra et al. | 422/65 |
| 6,013,168 A | 1/2000 | Arai | 204/601 |
| 6,199,435 B1 * | 3/2001 | Wilmer et al. | 73/864.14 |
| 6,207,031 B1 * | 3/2001 | Adourian et al. | 204/451 |
| 2001/0005489 A1 | 6/2001 | Roach et al. | 422/99 |

* cited by examiner

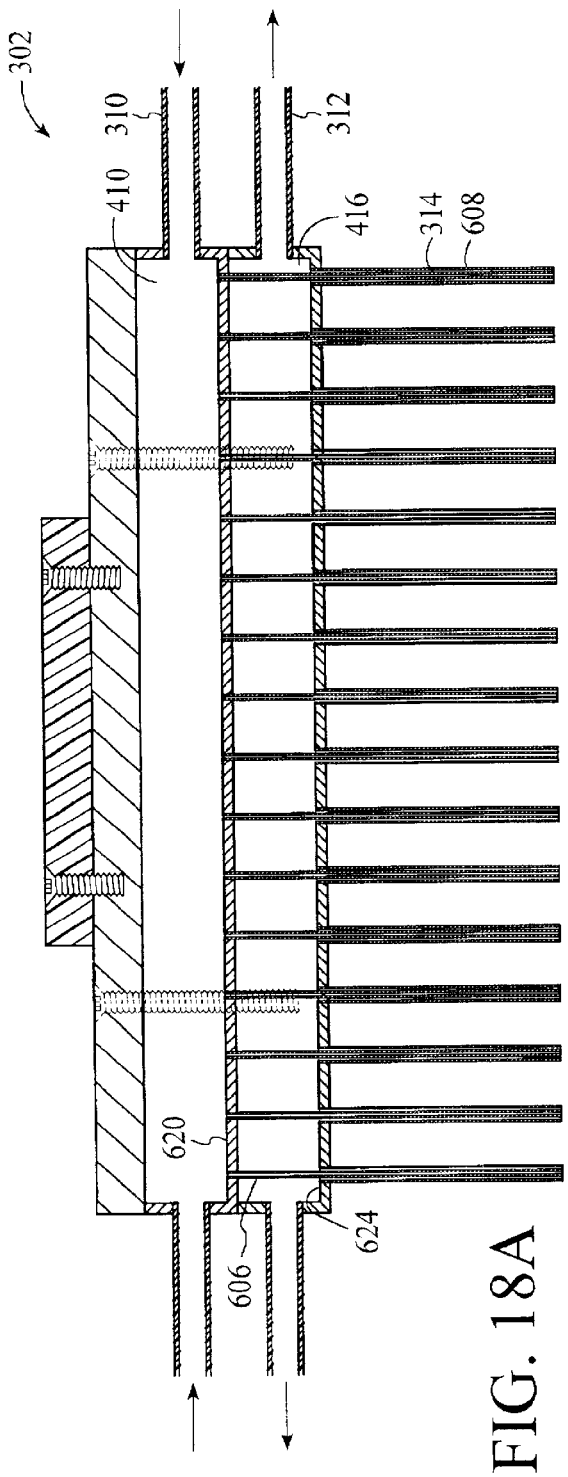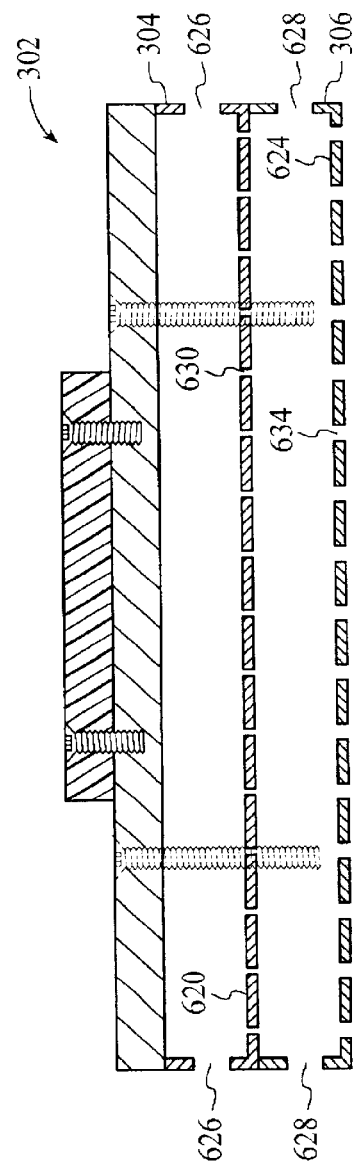
FIG. 18A
FIG. 18B

APPARATUS AND METHOD FOR FILLING AND CLEANING CHANNELS AND INLET PORTS IN MICROCHIPS USED FOR BIOLOGICAL ANALYSIS

CROSS-REFERENCE TO RELATED APPLICATIONS

This application is a continuation-in-part of application Ser. No. 09/556,897, filed Apr. 20, 2000 which is a divisional of application Ser. No. 09/109,676, filed Jul. 2, 1998.

TECHNICAL FIELD

The invention relates in general to molecular separation technology utilizing microchip substrates and in particular to an apparatus and method for filling and cleaning microchannels and inlet ports of microchip substrates for use and reuse in the molecular separation of samples.

BACKGROUND ART

In the past ten years or so, parallel capillaries have been used extensively for molecular separations, such as by means of electrophoresis. Capillary electrophoresis has been used for the analysis of DNA and proteins, and for the separation of small ions, small molecules, bacteria, and viruses. Different separation media have been used in the capillaries including solutions, gels, and polymers. In each technique, the mobility of the target can be measured.

Capillaries have been applied both to DNA fragment length analysis and to DNA sequencing. The study of nucleotide sequences relies upon the high resolution separation of polynucleotide fragments. Each fragment in a family of fragments is tagged with fluorescent markers and the differences in the molecular migration in a capillary channel are observed. Fragments having differences of only a single base pair are routinely separated with fluorescent detection.

To increase the throughput, many capillaries can be used in parallel. Parallel capillary electrophoresis allows many samples to be analyzed simultaneously and can result in high throughput rates.

Recently, several groups have implemented capillary electrophoresis in microchannel formats (A. T. Wooley, G. F. Sensabaugh and R. A. Mathies, "High-Speed DNA Genotyping Using Microfabricated Capillary Array Electrophoresis Chips", *Anal. Chem.*, 69:2181–2186 (1997); A. T. Woolley and R. A Mathies, *Anal. Chem.*, 67:3676–3680 (1995); A. T. Woolley, P. C. Simpson, S. Liu, R. Johnston, G. F. Sensabaugh, A. N. Glazer, and R. A. Mathies, "Advances in Microfabricated Integrated DNA Analysis Systems", *HPCE*98 (1998); P. C. Simpson, D. Roach, A. T. Woolley, T. Thorsen, R. Johnston, G. F. Sensabaugh, and R. A. Mathies, "High-throughput genetic analysis using microfabricated 96-sample capillary array electrophoresis microplates", *Proc. Nat'l. Acad. Sci. USA*, 95:2256–2261 (1998)). This approach uses microchannels etched or molded into a substrate as the separation channels in place of capillaries (R. M. McCormick, R. Nelson, M. G. Alonso-Amigo, D. J. Benvegnu and H. H. Hooper, "Microchannel electrophoretic separation of DNA in injection-molded plastic substrates", *Anal. Chem.* 69:2626–2630 (1997); U.S. Pat. No. 5,376,252, issued 1994 to B. Ekstrom, G. Jacobson, O. Ohman and H. Sjodin). The resulting device is commonly called a microchip, even though the physical size of the entire substrate can vary from microchip size, i.e. dimensions of a few millimeters on a side, to wafer size, i.e. dimensions similar to semiconductor wafers (10–20 centimeters diameter) to microchannels in 48 cm long "macrochips" (C. Davidson, J. Balch, L. Brewer, J. Kimbrough, S. Swierkowski, D. Nelson, R. Madabhushi, R. Pastrone, A. Lee, P. McCready, A. Adamson, R. Bruce, R. Mariella and A. Carrano, "Development of a Microchannel Based DNA Sequencer", *DOE Human Genome Program Contractor-Grantee Workshop VI*, Santa Fe, N.M. (1997)). The determining factors in microchip size are the complexity of microchannel routes and the lengths of the separation channels. The length of the channels must allow for sample input, sample migration and a measurement zone. The channels are typically of dimensions from 8 to 40 micrometers deep and 20 to 150 micrometers wide. The small channels resolve DNA fragments in significantly shorter times than capillaries with larger cross-sectional areas.

Beyond providing parallel capillaries, some advances in speed of analysis have been achieved by providing parallel sample wells and providing automated optical detectors and software analyzers.

In spite of these advances, fine separations are still a time consuming and labor intensive process, particularly when it comes to the preparation of the microchip substrate. Such preparations involve injection of separation media and solutions in the microchannels of the microchip substrate, filling inlet ports with solutions needed for analysis of samples, and cleaning the microchannels and inlet ports of the microchip substrate.

Prior art methods of filling and cleaning the microchannels and inlet ports of the microchip substrates involve a completely manual process. Matrix or other separation media is injected by syringe into common openings called anodes leading to the microchannels of the microchip substrate. The pressure of the matrix injected into the common anodes forces the old matrix out of the microchannels into a plurality of inlet ports on the microchip. Next, a pipette tip attached to a vacuum source is used to suction out solution or old matrix from the inlet ports one at a time. Sometimes, it is necessary to first add water to each of the individual inlet ports in order to dissolve any dry matrix so that it may be suctioned. Not only is this method time consuming, matrix in some of the microchannels may dry before all of the microchannels have been injected with new matrix. A dry matrix does not provide the electrically conductive path or the sieving characteristics necessary for proper separation of samples and is difficult to remove. Washing out the chip for storage involves a similar process in that each inlet port and all microchannels must be washed and dried individually. Although more microchannels present in the microchip substrate allow for more samples to be analyzed simultaneously, the preparation time of the entire microchip substrate increases.

An object of the invention was to devise an apparatus and method for efficient filling and cleaning of microchannels and inlet ports of microchip substrates for use in molecular separation and chemical analysis of samples. A further object was to automate the preparation of microchip substrates and to integrate the apparatus with the apparatus for the automatic handling and presentation of specimens into the microchips for parallel high throughput analysis in microchannels.

SUMMARY OF THE INVENTION

The above objects have been achieved with an apparatus for simultaneously cleaning and filling a large number of inlet ports and channels of a microchip substrate for use in molecular separations and chemical analysis of samples.

The microchip has macroscale inlet ports leading to the microchannels. The inlet ports are spaced apart to match the size and spacings of pipettors in an array of ganged pipettor tips.

The microchannels provide microscopic volumes, much less than a microliter, in which analysis is carried out. The instrument features a microchip handler, with relative motion of the microchip with respect to a pipettor, electrodes, and detector. In some instances the microchip is moved, while in other instances, the other components are moved. There is a sequence of automatic operations involving placing a sample-free microchip on a chuck, loading samples with a pipetting device into the microchip, contacting microchannels in the microchip with electrodes, injecting samples into the separation microchannels, running an electrophoretic separation, detecting and measuring the separation, and then removing the microchip. In a preferred embodiment, a microchip, pre-filled with matrix or other separation media but not sample, is held in a vacuum chuck which is movable with high precision on a first Y-axis track from a sample loading station to a sample analysis station.

In a preferred embodiment, the microchannels of the microchip are filled beforehand with matrix or other separation media that acts as a sieve to enhance sample separation. If the microchip substrate has already been used for molecular separation and chemical analysis and is in need of cleaning, an apparatus is used to clean and vacuum the inlet ports and to pump out the old matrix within the microchannels to the inlet ports for vacuuming before filling the microchip with new matrix. If the microchip substrate has not previously been used, the apparatus may be used to inject regeneration fluids, separation media or other solutions into the microchannels or solutions necessary for chemical analysis of samples into the inlet ports.

The apparatus has a manifold comprising six compartments. An upper chamber of the manifold is comprised of three compartments and a lower chamber of the manifold is comprised of three compartments. The three upper compartments each have opposed openings on each side for a total of six openings. Supply tubing which communicates with containers of solution is connected to the upper compartment openings. The three lower compartments each have opposed openings on each side for a total of six openings. Supply tubing which communicates with a vacuum source is connected to lower compartment openings. A plurality of openings on a lower surface of the upper chamber compartments and on lower surface of the bottom chamber compartments of the manifold are present for insertion of a tube-in-tube assembly.

The tube-in-tube assembly comprises a plurality of pressure tubes, surrounded by a plurality of vacuum tubes. The tube-in-tube assembly emerges from the manifold and engage the inlet ports of the microchip substrate. The apparatus also comprises a pressure injector manifold used to inject solution or matrix through the anodes or common openings of the microchip substrate leading into the microchannels of the microchip substrate. Old matrix is pumped out of the microchannels, if present, as new matrix or solution is pumped in. Wash solutions are pumped through the tube-in-tube assembly via supply tubing that communicates with the containers of solution. Solutions or matrix present in the inlet ports of the microchip substrate are vacuumed by the vacuum tubes of the tube-in-tube assembly which are connected to supply tubing that communicates with the vacuum source.

The apparatus may be automated and integrated with the apparatus for the automatic handling and presentation of specimens into the microchips for parallel high throughput analysis in microchannels.

At the sample loading station, samples can be loaded into the microchip by a multifunctional device, that includes a pipettor. The multifunctional device moves along a transverse X-axis gantry between the sample loading station on the first Y-axis track and tip and sample stations both on a second Y-axis track, parallel to the first Y-axis track. The second track can move pipette tips, reagent trays, microtiter trays containing samples, or other objects automatically into position for use by the multifunctional device. The multifunctional device, carried by the gantry, moves up and down on a Z-axis, perpendicular to the X and Y axes. Motion along all axes is driven by stepper motors so that precise and accurate positioning may be achieved. A servo motor or other actuator systems may be used for precise position control.

The multifunctional device contains a plurality of ganged pipettors, an individual pipettor, and a vacuuming line. The plurality of pipettors is ganged with spacings matching the well spacings on a microtiter plate. The same spacings are used for sample loading inlet ports on the microchip. In this manner, a multiple-channel pipettor can simultaneously load multiple samples into sample inlet ports.

The multifunctional device can be moved initially to the tip and sample stations on the second track where new pipette tips are applied to the ganged pipettors. The multifunctional device then moves on the gantry to pickup a tip guide and then moves back to the tip and sample stations on the second track. The second track can then be moved to a position where the ganged pipettors on the gantry can withdraw samples from a microtiter plate on the track. The multifunctional device then moves on the gantry to the sample loading station where it deposits the samples into sample inlet ports in the microchip on the first track. The multifunctional device moves back along the gantry first to release the tip guide and then to the tip and sample station where the used tips are discarded into a used tip tray that has been moved into position below the multifunctional device by the second track. The cycle of picking up tips, tip guide, and samples; delivering the sample to the microchip; and then parking the tip guide and discarding the used tips is repeated until the microchip has been completely loaded.

After the microchip has been loaded, it is moved to the sample analysis station on the first track below a sample analysis detector and raised to dock with the array of wire electrodes supported by a platform over the first track. The final position of the microchip places the microchannels in the focal plane of a detector at the sample analysis station. The detector preferably includes a scanning confocal laser microscope capable of detecting fluorescently tagged molecules during separation.

The electrical potential of the electrodes can be controlled to first move precise sub-microliter volumes of the samples from the loading wells into an injection region of the separation microchannels, and then to stimulate electromigration in the separation microchannels.

As the samples separate in the microchannels, a region of the microchip is monitored, typically by a scanning confocal laser microscope to detect the molecular separations. For DNA sequencing, four fluorescent markers are usually detected for forming four-color electropherograms of the separations. The four-color electropherograms can be processed to ultimately call the bases and determine the DNA sequence of the samples.

BRIEF DESCRIPTION OF THE DRAWINGS

FIG. 18(a) is a cutaway view of the manifold of FIG. 16.

FIG. 18(b) is a cutaway view of the openings of a compartment of the manifold of FIG. 16.

BEST MODE FOR CARRYING OUT THE INVENTION

Figure 1:
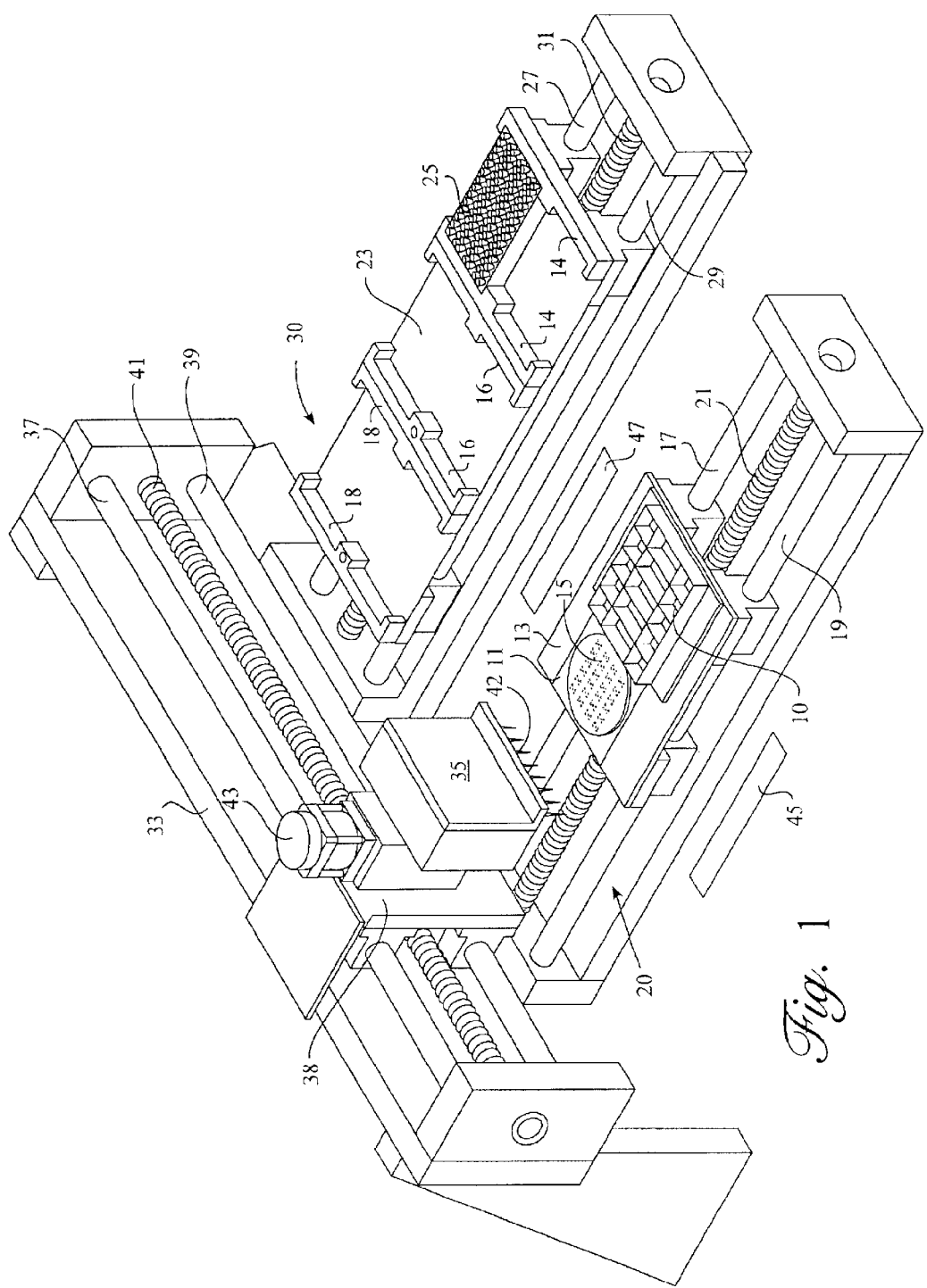
FIG. 1 is a perspective view of the apparatus for the automatic handling and presentation of specimens into the microchips for parallel high throughput analysis in microchannels, without a sample analysis detector, tip counter, or tip guide.

With reference to FIG. 1, a robotic instrument for microchannel chemical analysis is seen featuring two parallel tracks 20 and 30, with a gantry 33 spanning the parallel tracks. The tracks, 20 and 30, and the gantry 33 are Parker Daedal linear translation stages, well known in the semiconductor equipment field. The first track 20 aligned along a Y-axis, has parallel rails 17 and 19 having a leadscrew 21 midway between. The screw 21 is a precision screw driven by a stepper motor so that a first frame 13, which rides on rails 17 and 19 by means of roller bearings, may be positioned in a desired location. The motor driving the screw is not shown. The roller bearings make contact with the rails 17 and 19 from the first frame 13. By turning screw 21 the first frame 13 may be precisely positioned in a desired location, such as below the multifunctional device 35.

The frame carries a substrate chuck 11, also known in the semiconductor industry as a vacuum chuck for securely holding semiconductor wafers. The substrate chuck 11, adjacent to electrode washing station 10, holds a disk-shaped microchip substrate 15 having microchannels thereon.

As used herein, the term microchip refers to a substrate that contains microchannels. The microchip of the present invention is typically much larger than an integrated circuit microchip. Microchip 15 is shown to be the size of a glass or silicon wafer, with a diameter of about four inches, although larger or smaller devices, or other shapes, may be used. It is not intended that the present invention be limited to any particular size or shape of substrate with microchannels. It is further not intended that the configuration of the microchannels on the microchip be limited to any particular design, but rather that it encompass any geometries, including both two- and three-dimensional microchannels.

As used herein, the term microchannel refers to any channels with cross sectional linear dimensions of less than a millimeter. The microchannels typically have a width in the range of 30 to 150 micrometers and a depth in the range of 5 to 50 micrometers. The microchannels are typically defined therein by microchip manufacturing technology, i.e. masking and etching, although other techniques comprising embossing, micromolding, deposition, and other microfabrication technologies can also be used.

The second track 30, also aligned along a Y-axis, has parallel rails 27 and 29. These rails support the second frame 23 in a low friction rolling relationship. A screw 31 drives the second frame. The second frame carries the microtiter plate 25 as well as other racks or plates which may be seated in holders 14, 16, and 18.

Gantry 33 is a third track, aligned along an X-axis, perpendicular to the Y-axes, having parallel rails 37 and 39, carrying third frame 38 which supports a multifunctional device 35. Screw 41, turned by a stepper motor, not shown, moves the third frame 38 and the multifunctional device 35 between the first track 20 and the second track 30. The multifunctional device functions as a robotic arm carrying a pipettor assembly with a ganged pipettor, an individual pipettor and a vacuum device or other devices.

The multifunctional device 35 can move in the Z-axis, perpendicular to the X and Y axes. Motor 43 moves the multifunctional device 35 with up and down motion in the Z-axis. This motion is used to lower the pipette tips 42 held by the multifunctional device 35 into the microchip, the microtiter plate 25, or the pipette tip racks. The movable pipette tips may be lowered for insertion into the microtiter plate to withdraw samples, then are lifted and moved on the gantry to the first track without interference where they make contact with the microchip for sample loading.

Not shown in FIG. 1 is a detector or measurement instrument, such as a scanning confocal laser microscope, that is located on a platform that stands on pedestal pads 45 and 47, on opposite sides of the first track. The detector sits on a platform above the first frame 13 and is used to induce fluorescence and collect the fluorescence light from microchannels on the microchip.

Figure 2:
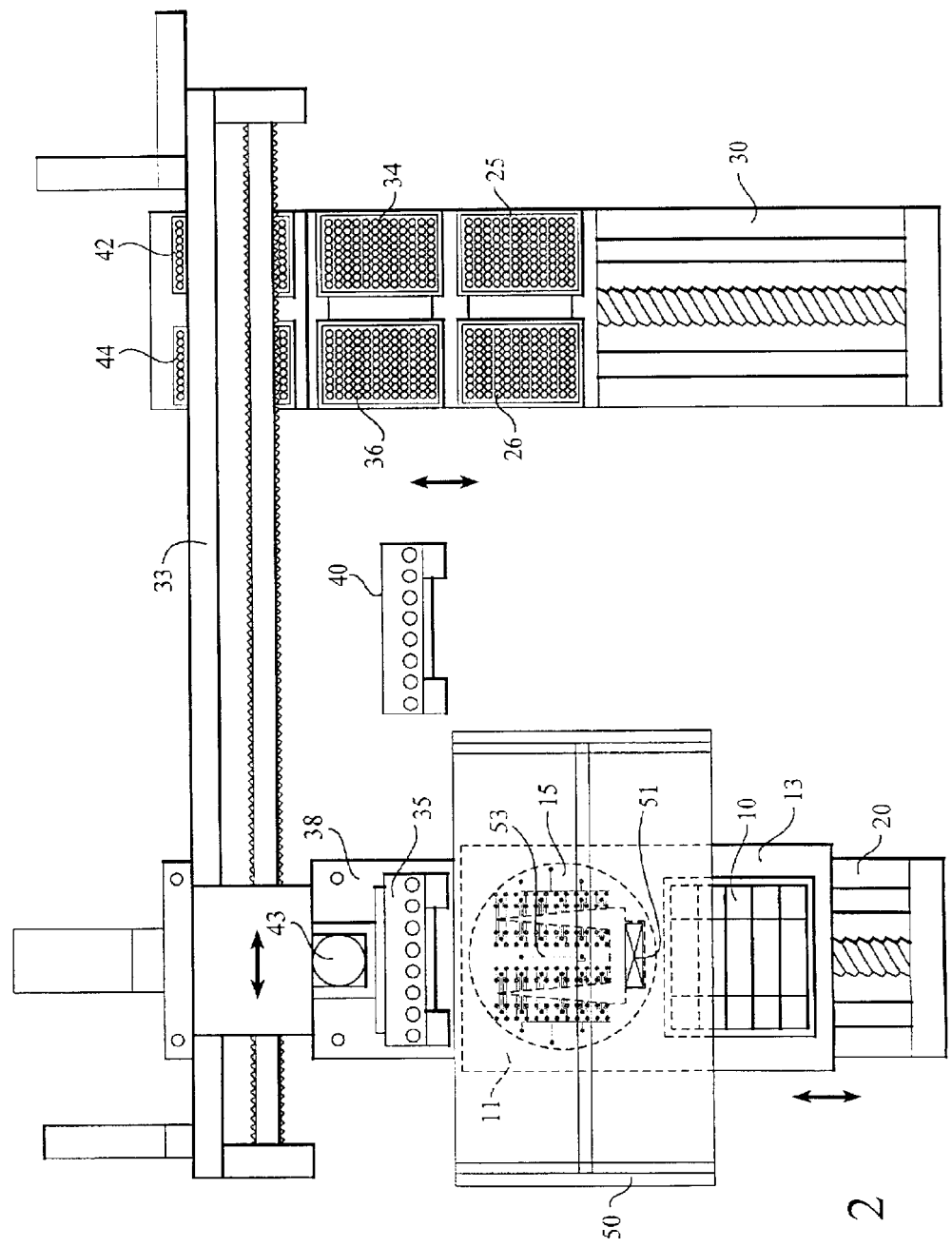
FIG. 2 is a top view of the apparatus of FIG. 1, with a sample analysis detector and tip guide.

With reference to FIG. 2, the first track 20 is spanned by a platform 50, standing on the previously mentioned pedestal pads. The platform 50 carries the array of electrode wires and a sample analysis detector such as a scanning confocal laser microscope. The first frame 13 is advanced to the position of multifunctional device 35 where an array of pipettors carried on the multifunctional device 35 which is attached to third frame 38 dispenses sample material into inlet ports within microchip 15. The pipettors can move up and down along the Z-axis and in a lowered position dispense sample into holes in the microchip. Up and down motion is controlled with the stepper motor 43 which takes the pipettor assembly to its target position. An air cylinder on the multifunctional device actuates the pipettor of interest thereby dispensing samples into the microchip.

The multifunctional device 35, carrying the pipettor array, is movable to the vicinity of the second track 30 where the microtiter plates 25 and 26 reside, as well as fresh pipettor tips in racks 34 and 36. Used tips may be discarded in tip waste racks 42 and 44. The pipettor array on the multifunctional device uses a second air cylinder for attaching new tips and ejecting used tips from the pipettors. After moving to a waste tip rack, the air cylinder behind the pipettor bodies of the pipettor assembly is engaged to push tips off the individual pipettors. To pick up tips, the pipettor assembly is moved over a new tip tray. Then, the stepper motor 43 lowers the multifunctional device 35 near the pipette tips where the air cylinder raises and then abruptly lowers the pipettor assembly with respect to the multifunctional device 35 and provides a spring action to ensure tip pickup from the new tip tray by pushing the tips onto the pipettors. The new tips are held in place by friction engagement.

A second air cylinder actuates the pipettor to pickup and deliver fluids. More material is picked up than is dispensed, thereby reducing the possibility of forming bubbles in the well. Bubbles would interfere with proper current flow in the microchannels.

A tip guide 40 is positioned between the second track 30 and the first track 20. Tip guide 40 is a block having an array of conical holes for allowing entry of pipettor tips. The tip guide is held onto the multifunctional device by vacuum. The tip guide positions tips on the pipettor for precise alignment with the holes in the microchip. The use of the tip guide is optional and is dependent on the design of the microchip.

Figure 3:
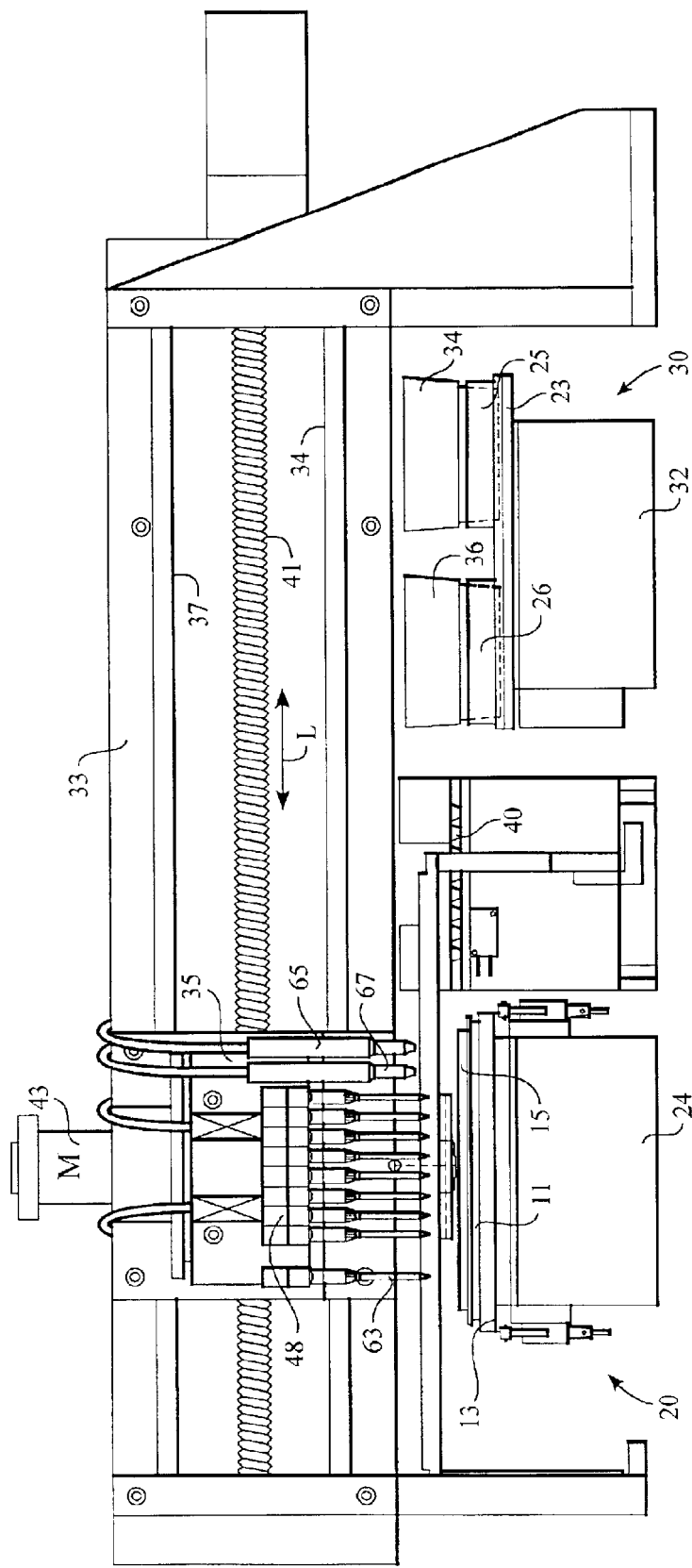
FIG. 3 is a front plan view of the apparatus of FIG. 1 with a tip guide.

With reference to FIG. 3, the first track 20 may be seen to be mounted on a first support table 24 with first frame 13 carrying the substrate chuck 11 and microchip 15 atop the chuck. Multifunctional device 35 is mounted for up and down motion so that pipettor tips can enter holes in the substrate. Gantry 33 allows positioning of the multifunctional device 35 with respect to the first track 20, the tip guide 40, and the second track 30. The second support table 32 holds a second track 30 that carries a second frame 23 bearing microtiter plates 25 and 26, as well as pipette racks 34 and 36. The multifunctional device 35 may move laterally and communicate with microtiter plates 25 and 26. Optical and mechanical position sensors locate the frames on the first and second tracks with respect to the pipettor assembly of the multifunctional device. The controller for the multifunctional device must ascertain the exact positions of the substrate chuck on the first frame, as well as the microtiter plate on the second frame in order to receive and deliver samples to the correct locations.

The multifunctional device 35 is shown to have several other features. It can use a single channel pipettor 63, spaced slightly away from the linear array of ganged pipettors in pipettor assembly 48 to pipette liquids into or out of wells that are not necessarily at the spacings of the ganged pipettor. It has a suction line 65 to remove samples or matrix from the microchip, and a pressure line 67 to move matrix or to facilitate sample injection as needed. In addition, the multifunctional device 35 can accommodate other means of moving sample into the microchip, such as using a pipetting device with capillaries, microbore tubing, or volumetric devices. The multifunctional device 35 can also be adapted to access a reservoir for bulk pipetting of solutions. A piezoelectric delivery apparatus could also be added if required for precision volumetric control. It is within the scope of the invention that the microchips are loaded by an automated process from a plurality of microchips held in a rack, or hotel, or similar device and that the microtiter plates and racks of pipette tips are also changed by automated mechanisms.

Figure 4:
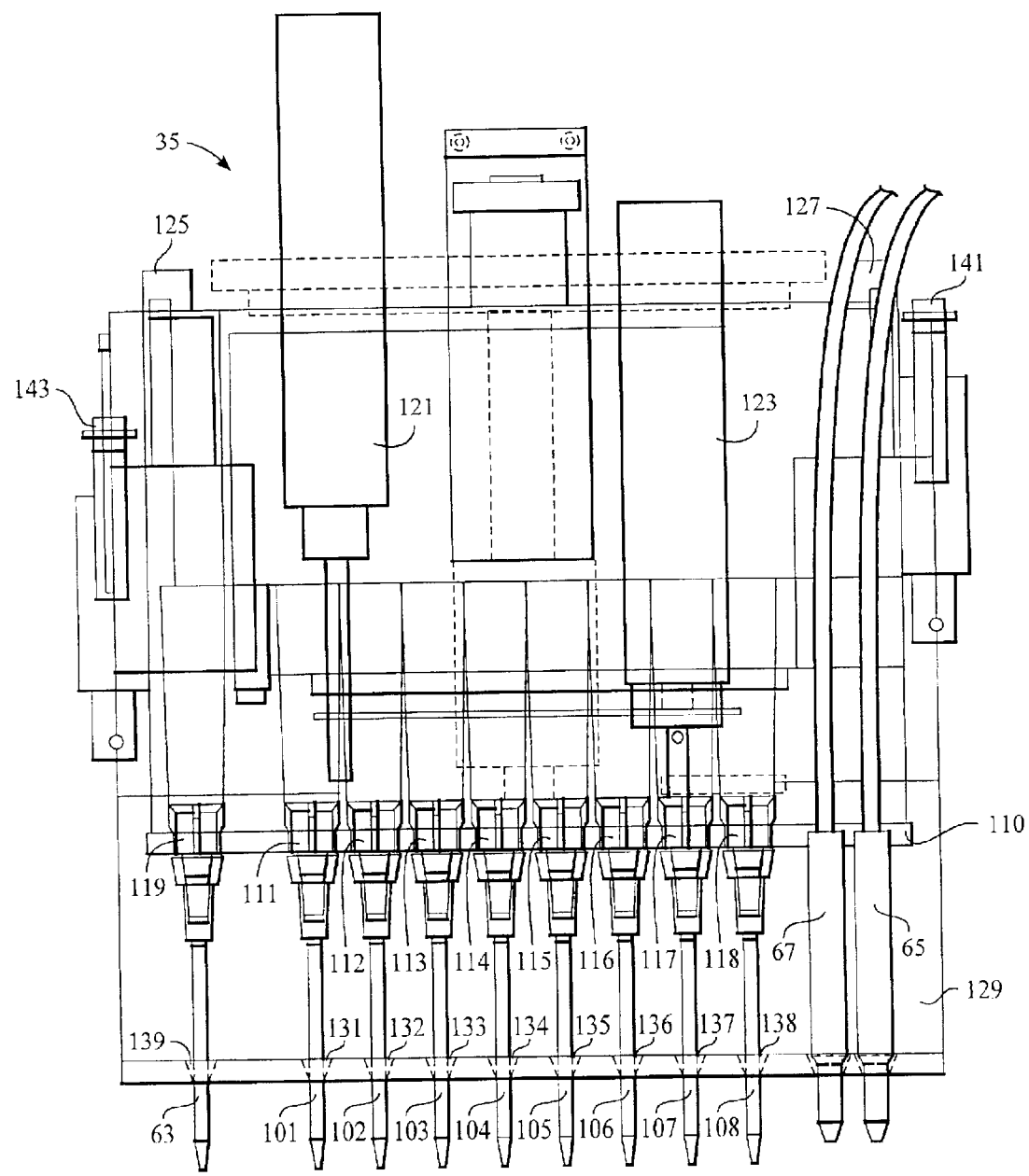
FIG. 4 is a detailed front view of a multifunctional device used in the apparatus of FIG. 1.

With reference to FIG. 4, the multifunctional device 35 is seen to carry an array of individual pipette tips 101–108, plus a single channel pipettor tip 63. When tips are picked up, one to all pipettors are fitted with tips. Each of the tips is connected to a fluid pipetting mechanism which may be a standard Eppendorf pipettor. The pipettors extend through a U-shaped tip ejector 110. The pneumatic cylinder 121 is controlled by an electronic controller for pipetting desired amounts of fluid, on command, through the array of tips 101–108. Microswitches 141 and 143 are mounted on opposite sides of tool 35, at two different elevations, for sensing whether the tool is high or low and signaling the position to other devices. A suction line 65 is mounted at the side of tool 35 for sample or matrix removal from a microchip. A pressure line 67 is used for matrix refilling or to assist with sample injection.

Tip ejector 110 is mounted for up and down motion on short rails with a pair of stops 125 and 127 limiting upward motion of the tip ejector. A pneumatic cylinder 123, connected to a controller, supplies the force for motion of the tip ejector. Tips are ejected when the pneumatic cylinder 123 attempts to raise the tips beyond the tip ejector 110 when tip ejector is stopped against the pair of stops 125 and 127. In this situation, the tips move upwardly, but are stopped against tip ejector 110 and fall off of the pipettor.

The multifunctional device 35 also carries a tip guide 129 which is held in place by suction supplied by a line, not shown, but which suction may be commanded on and off. The tip guide has apertures 131–139 so that the pipette tips are straight from respective pipettors outwardly toward a microchip inlet. The tip guide is an assembly that is picked up from a special location after fresh tips have been attached onto the pipettors, but before the tips are used to withdraw samples from a microtiter plate. Similarly, the tip guide is released before used tips may be discarded into a used tip holder or tray.

Figure 5:
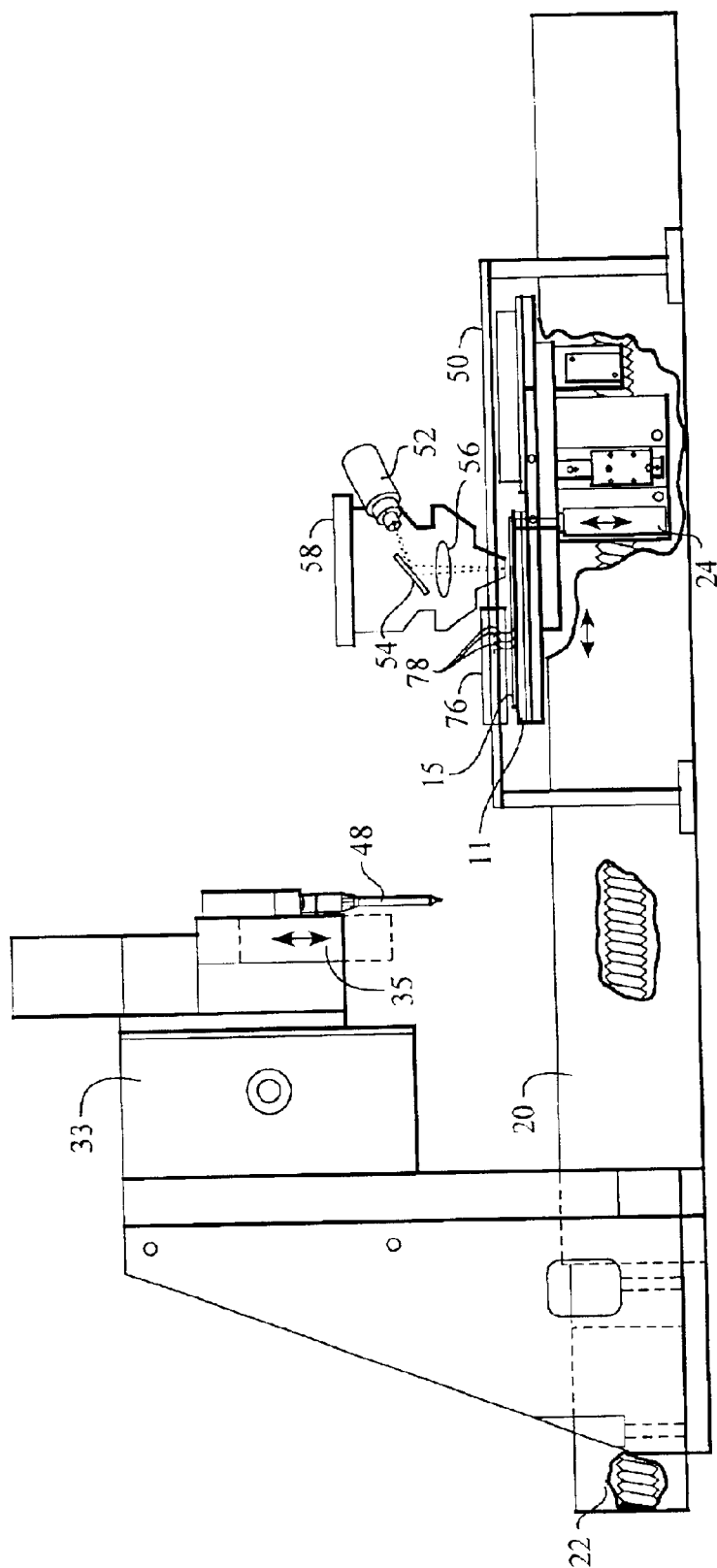
FIG. 5 is a left side view of the apparatus of FIG. 1, with a cutout of the sample analysis station and the detector.

With reference to FIG. 5, at the time of introduction of sample material into microchip 15, the microchip 15 and chuck 11 are moved directly below the pipettors 48 by means of track 20 and its stepper motor and then the pipettor tips 101–108 are lowered into holes in the microchip to deliver sample material. Hole patterns in the microchip match the spacing of tips in the pipettor array, when an array is used. The substrate is able to move under the multifunctional device to different locations using a stepper motor in housing 22 associated with track 20 so that sample material may be delivered to entry holes at various locations.

The microchannels in the microchip are preferably grouped into rows and have eight apertures per row. This allows the array pipettor on the multifunctional device to feed multiple microchannels simultaneously. It is advantageous that sample be delivered simultaneously to eight to twelve, perhaps more, or all sample locations simultaneously until all microchannels have sample. This considerably speeds sample loading for the multiple microchannels. For example, if there are 96 microchannels and 8 pipettor tips, the substrate will need to be moved at least 12 times so that all microchannels will be equipped with sample material. Moreover, the pipettor may need to move laterally while the substrate moves to a position on track 20 so that the pipettor tips will fit into the desired holes in the substrate.

After loading of all the samples, the microchip is then moved to an appropriate position under platform 50. The substrate chuck 11 is raised by pneumatics 24, and an array 78 of fine wires used as electrodes protruding from a circuit board 76, mounted on the underside of platform 50, is automatically inserted into apertures in the microchip. The fine wires are self-supporting stiff wires resembling wafer probe wires used in the semiconductor industry and are used as cathodes and anodes for the separation and to provide other voltages to the microchip. Usually such wires are platinum or other materials with good electrical conductivity and corrosion resistance with diameters typically from 200 micrometers to 500 micrometers.

When certain of the electrodes are connected to appropriate voltage sources, samples can be moved from the sample inlet ports into the separation channels using an electric field; this movement is also referred to as sample injection. The voltage sources are then changed to separate the samples by means of electrophoresis. Typically the microchannels have been pre-loaded with an appropriate separation medium. For example, a separation matrix comprising hydroxyethyl cellulose (HEC) in combination with urea and formamide is disclosed in U.S. Pat. No. 5,534,123 by J. Bashkin, D. Barker and R. Johnston, assigned to the assignee of the present invention.

Once sample migration occurs, the detection region on the microchip is monitored. For fluorescence detection, the excitation light source 52 is selected to have a wavelength that will stimulate fluorescence from target tags. For scanning confocal laser microscope detection, the laser beam excitation light is directed to a galvanometer-based scan mirror 54 that scans the microchip through an objective lens 56, commonly known as a "macro scanning objective". Such objectives have been described for scanning large fields of fluorescent samples; for example, a fluorescence imaging system is described in U.S. Pat. No. 5,719,391 by Robert Kain and assigned to the assignee of the present invention. The objective lens collects emitted fluorescent light from fluorescently tagged target molecules under electrophoretic migration in the microchannels. After intermediate optics, such as a confocal spatial filter and filters to select appropriate wavelengths, photomultiplier tubes 58, CCD arrays, or other photodetectors convert this fluorescence light to electric signals which are collected and processed to form electropherograms.

Figure 6:
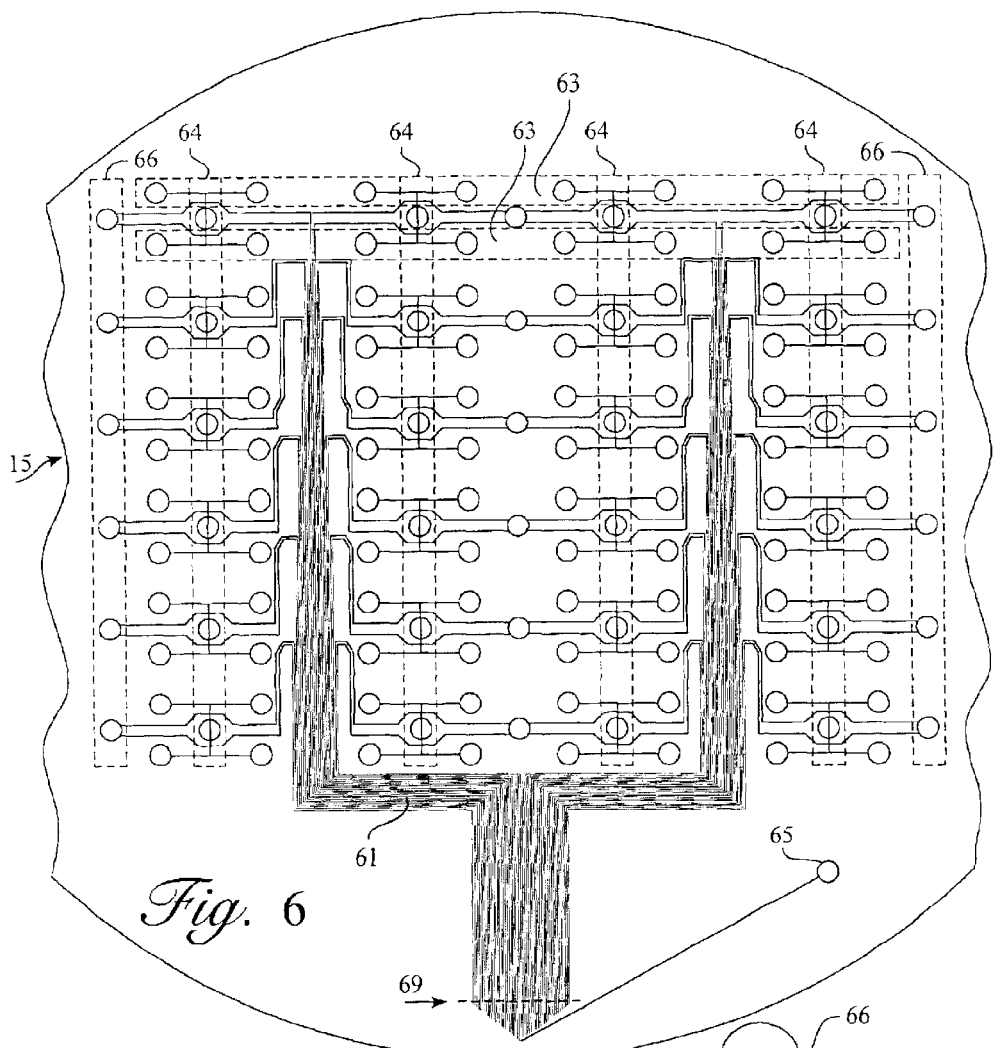
FIG. 6 is a magnified top view of a microchannel structure on a microchip for use in the apparatus of FIG. 1.

With reference to FIG. 6, the microchip 15 is seen to have a plurality of separation microchannels 61 formed in one plate that has been bonded to another plate, not shown. By way of background information, this microchip 15 has been described in P. C. Simpson, D. Roach, A. T. Woolley, T. Thorsen, R. Johnston, G. F. Sensabaugh, and R. A. Mathies, "High-throughput genetic analysis using microfabricated 96-sample capillary array electrophoresis microplates", *Proc. Natl. Acad. Sci. USA*, 95:2256–2261 (1998). The channels have a bottom plate so that fluid cannot escape. The microchannels terminate in open apertures 66 that are used as cathode reservoirs. These reservoirs can either be for each channel or, as shown, may service multiple microchannels. The sample loading reservoirs or inlet ports, two rows being shown in dashed rectangular rows 63, can be large enough for a pipettor tip to enter in order to deliver sample.

In a preferred embodiment, the sample loading reservoirs 63 are connected to waste reservoirs, shown in the dashed rectangular columns 64, by injection microchannels that cross the separation microchannels, as described below. The ends of the separation microchannels merge into a common anode reservoir or port 65, that is accessible through a hole in the top of the microchip. The sample loading reservoirs or inlet ports 63, waste reservoirs 64, anode reservoir 65, and cathode reservoirs 66 are either individually contacted with electrode wires when the microchip is raised into position or each is individually contacted with electrodes plated onto the surface or within the center of the microchip, terminating at electrically conductive connectors positioned on the edge of the microchip, as shown in FIG. 7.

Figure 7:
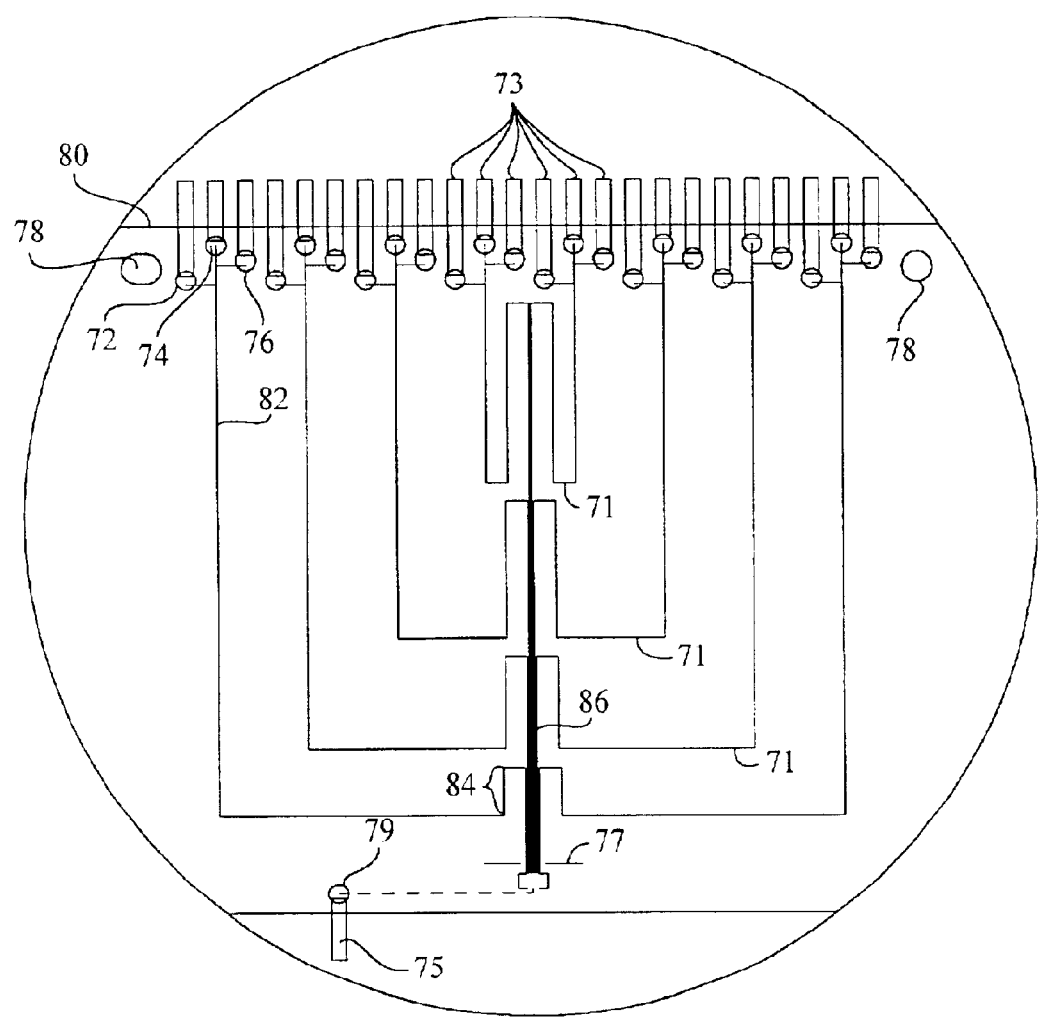
FIGS. 7 and 8 are top views of two alternate embodiments of the structure shown in FIG. 6.

In a preferred embodiment for DNA fragment analysis shown in FIG. 7, the separation microchannels can contain sharp turns 71. While these turns introduce band broadening, the effect is acceptable in a fragment analysis application, such as genotyping. The sharp turns can be used to increase the channel density to up to at least 48 separation channels on a 4" microchip, and can be used to equalize path lengths.

FIG. 7 also illustrates the incorporation of edge electrically conductive connectors 73 and 75 into a microchip. Edge connectors 73 and 75 may be formed by the vapor deposition of metal, such as gold, platinum, or copper, onto glass after the microchannels have been etched, using masking and deposition techniques well known in the semiconductor industry. The edge connectors are flat tabs, like electrical circuit board edge connectors. The edge connectors serve as electrodes and simplify the electrical connection from the microchip to the macroscale. Line 80 indicates where the cover over the substrate terminates, allowing access to the electrical connectors from outside. Below line 80, the substrate has a cover over the electrical terminals where the terminals are not accessible, except through entry ports 72, 74, 76 extending through the cover. A portion of the edge connectors 73 are cathode terminals, while edge connector 75 is an anode terminal. Triplet arrangements of entry ports 72, 74, 76 allow sample movement across a portion of the main microchannel 82 for purposes of injecting sample into the microchannel 82. Microchannel 82 has path bends 84, leading to a main trunk 86 where all microchannels are brought into a parallel array.

In a preferred embodiment, fluorescence detection takes place at scan line 77, an imaginary line, not far from anode port 79 using a scanning confocal laser microscope. Laser scanning at scan line 77 is transverse to the microchannels in the parallel array. Locator holes 78 are used to position the microchip in a desired location.

Figure 8:
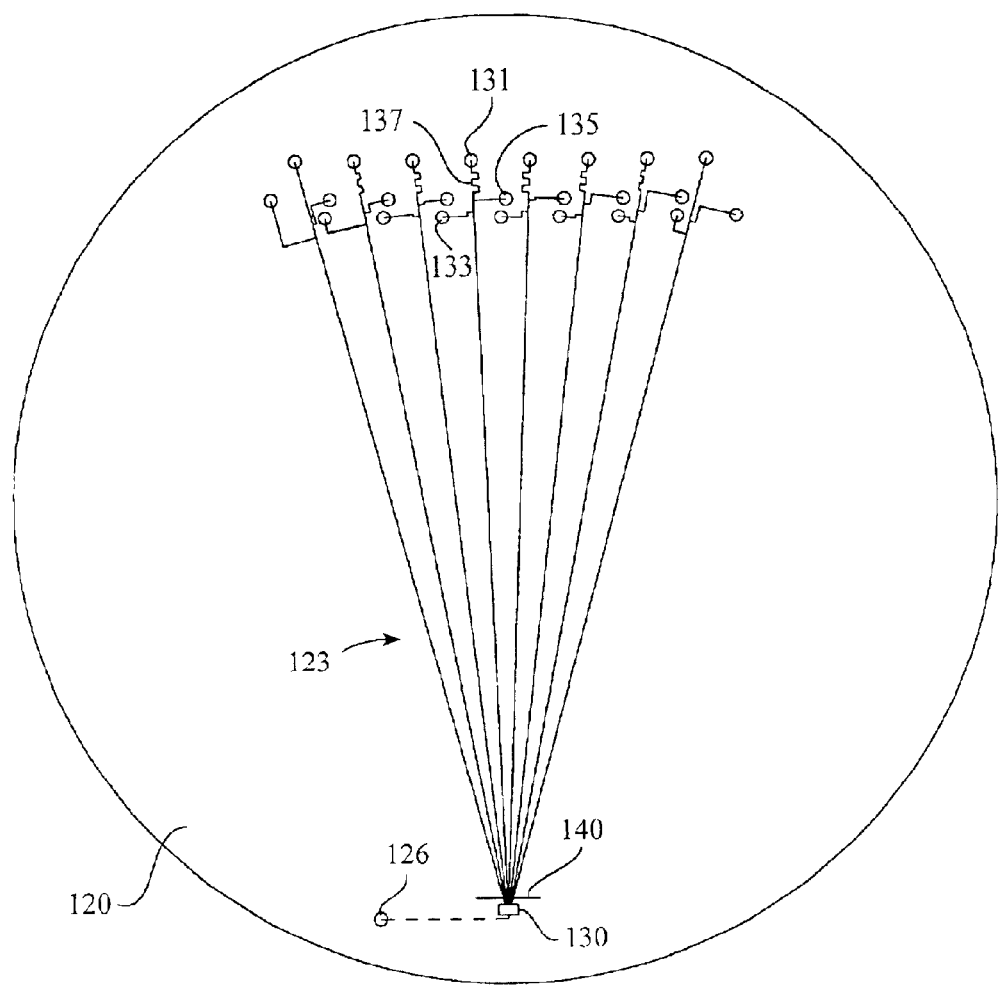

With reference to FIG. 8, a microchip 120 has radially distributed microchannels 123 with a spoke-like pattern considering collector 130 as a hub. The number of microchannels is governed by the size of the microchip. A large array could have microchannels in a 360 degree pattern around a common collector. The microchannels are etched into a glass wafer which is covered with a second flat wafer of similar or identical diameter. Each radial microchannel converges toward a collector 130. The collector is an end reservoir connected to an anode port 126 where an electrode may be inserted. A scan line 140 is an imaginary line where a scanning beam will traverse the converging microchannels, very near the collector 130. The beam, typically a laser beam, will excite fluorescence in the microchannels and the emitted fluorescence will be measured by a detector. Each microchannel has a triplet of inlet ports 131, 133 and 135 for the cathode, waste, and sample reservoirs respectively. The path undulations 137 are introduced for the purpose of path length equalization so that all paths are the same length for electromigration purposes.

A radial configuration of microchannels has the advantages that no bends or turns are present between the injection region and the detection region. The bends or turns degrade the separations and may preclude the high resolution separations required for DNA sequencing.

Figure 9:
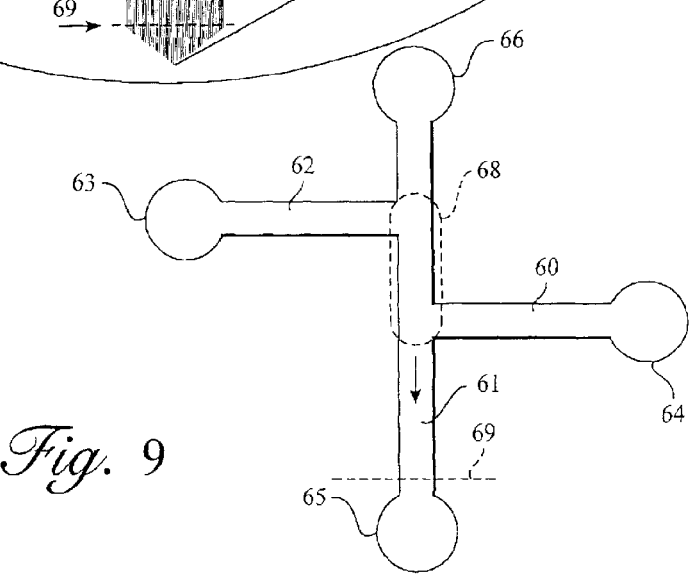
FIG. 9 is a simplified diagram of microchannel paths in the microchips shown in the FIGS. 6–8.

In FIG. 9, a detail of the injector and triplet of inlet ports, shown in FIGS. 6–8, is magnified. Sample reservoir 63 may be seen to have a microchannel path to the waste reservoir 64. Each reservoir has an opening of about 1.4 mm. in diameter at the surface of a microchip, leading into a microchannel. After all of the samples are loaded in the loading reservoirs 63, samples are moved through the stub microchannel 62 toward the waste reservoir 64 via the second stub microchannel 60 using an electrical potential between the loading reservoir and the waste reservoir. Alternative embodiments may use capillary action, pressure, magnetic, optical trapping, isoelectric focusing, and vacuum injection methods to move the samples into the separation microchannels. Typically, 3 to 5 microliters are inserted into the loading reservoir 63, but the injection region 68 volume only contains from 150 picoliters to 5 nanoliters. This microscopic volume is all that is separated in separation channel 61 under influence of the electric field.

The sequence of events for sample injection in a preferred embodiment is that an injection voltage is applied between each set of sample loading reservoirs 63 and waste reservoirs 64 with a biasing voltage applied to the anode reservoir 65 and cathode reservoirs 66 to prevent sample diffusion into the separation channels 61. The injection voltage is maintained until the sample has moved into the injection region 68 of the microchannels between sample loading reservoirs 63 and waste reservoirs 64 and the separation microchannels 61.

A separation voltage is then applied between the anode reservoir 65 and cathode reservoirs 66 while a back bias is applied to the sample loading reservoirs 63 and waste reservoirs 64 to prevent additional sample from entering the separation microchannels 61. The separation voltage is typically 50 to 300 V/cm and the back bias is typically 90 to 1000 V, depending upon channel lengths. The separation voltage is applied until the samples have passed scan region 69. A typical separation path length from injection region 68 to the detector at scan region 69 is ten centimeters. The detector is located as close as possible to the end of the straight portion of the separation channel 61 so that the maximum separation can be achieved. A typical separation time is five minutes for fragments and five to twenty five minutes for DNA sequencing.

It is preferable that all paths from the injection region 68 to the anode 65 have equal length and, further, that the paths from the cathode reservoirs 66 to the anode 65 have equal length and that paths from the sample loading reservoirs 63 to the waste reservoirs 64 have equal lengths.

An optical beam from the scanner sweeps across the scan region, illuminating the region and causing fluorescence of tagged target molecules. The scan area of the microchannels is that area where separations are best measured. Target molecules have been tagged with a dye or fluorescent material. When the target molecules are illuminated by the scanner, optical signals characteristic of the dye, fluorescent tags, or target material will be emitted and simultaneously measured by an optical signal detector. Multiple colors or wavelengths are used to distinguish different targets. Presently, for DNA sequencing, four colors are used, corresponding to four nucleotide bases, but any number may be used, depending on the ability of the detector to resolve the different colors, of the beam to generate the fluorescence, and the specific application. For genotyping, one or two colors are typically used, although more colors will allow more samples to be multiplexed per separation channel.

The microchannel arrangement of FIGS. 6–8 allows many channels to be scanned with a single beam scan across the scan region. The beam starts from a known or home position and illuminates each microchannel successively at a known rate of scan. By knowing the scan characteristics, the exact beam position is known and, hence, the identity of the illuminated microchannel is known. The beam spot size is typically ten microns, which is much smaller than the width of the microchannel. Since a large number of separations may be carried out simultaneously, there is a large time savings in analytical operations, such as sequencing. From separation data, the target sample may be identified.

The run is terminated by cessation of applying voltage to the electrodes, the data files are saved, and the vacuum chuck containing the microchip is lowered. The vacuum chuck with the microchip is then moved along first track 20 to the microchip installation position where the microchip is manually removed. The electrode wires are cleaned by moving first track 20, as shown in FIG. 2, until the wash station 10 is positioned below the electrodes. The wash station, containing a cleaning solution, is raised and lowered until the electrodes are cleaned.

Figure 10:
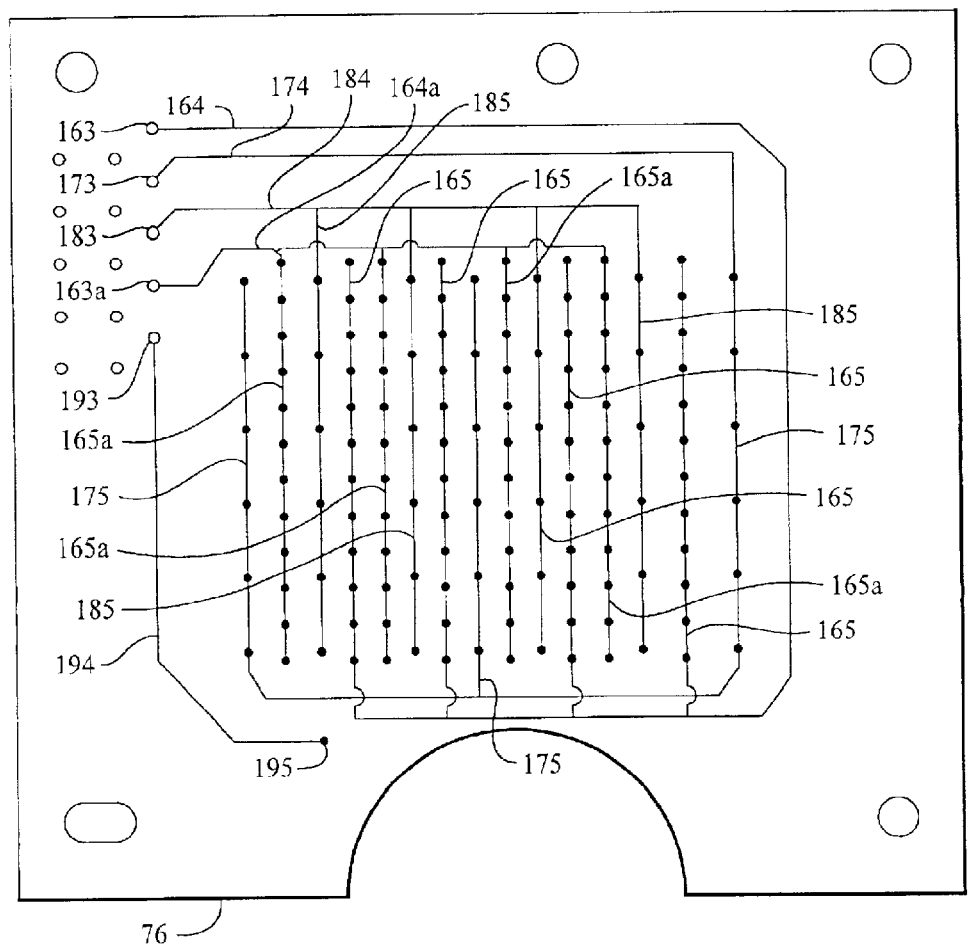
FIG. 10 is a plan of a circuit board showing electrode connections for use in the apparatus of FIG. 1.

With reference to FIG. 10, a circuit board 76 used to support electrodes from the platform over the first track is seen to have five independent wire (or trace) paths 164, 164a, 174, 184 and 194. Each path connects a power terminal to one or more electrode terminals, shown as round dots along a trace. Electrode terminals 163 and 163a are connected to wire traces 164 and 164a and to sample terminals 165 and 165a. Electrode terminal 173 is connected to wire trace 174 and to cathode reservoir terminals 175. Electrode terminal 183 is connected to wire trace 184 and to waste reservoir terminals 185. Electrode terminal 193 is connected to wire trace 194 and to anode reservoir terminal 195. Note that none of wire traces 164, 164a, 174, 184 or 194 intersect another wire trace, but that the wire traces are in mutually insulated relation. The electrode wires previously mentioned are connected to the sample terminals 165 and 165a, to the cathode reservoir terminals 175, to the waste reservoir terminals 185 and to the anode reservoir terminal 195, but are not shown in FIG. 10. The wires extend perpendicularly from the circuit board 76 in a self-supporting manner. The circuit board 76 is mounted so that the lower surface of the board is generally parallel with the underside of platform 50 immediately above the microchip to be used for migration measurements and immediately adjacent to the scan region of the microchip.

Appropriate voltages are applied to terminals 163, 163a, 173, 183, and 193. The same voltage appears over the length of each connected wire, because the voltage drop over the length of each trace is nil, i.e. the resistance of each trace is very small and only low currents are flowing.

The electronics consists of four modules: motion control, high voltage control, data acquisition, and miscellaneous.

Figure 11:
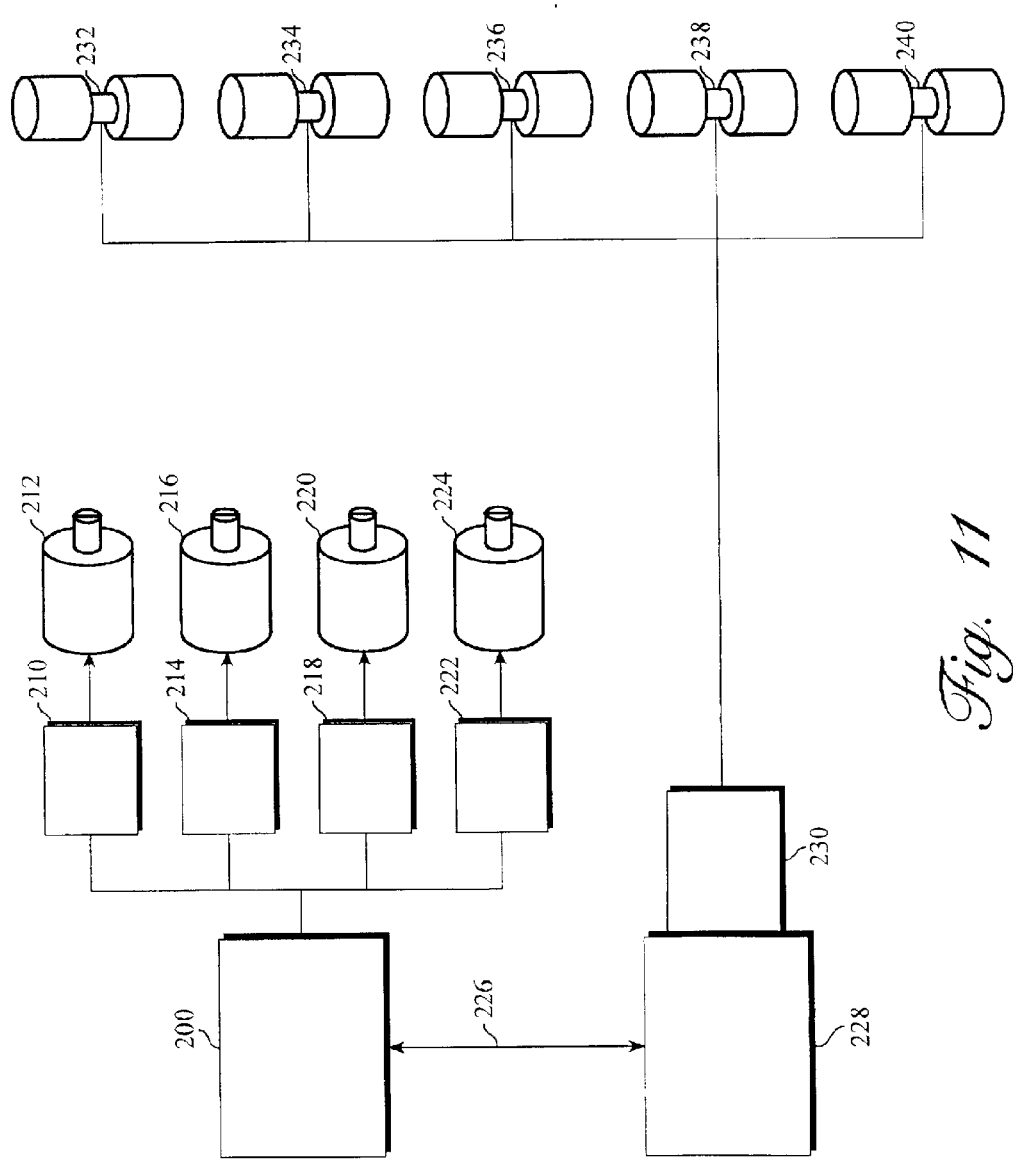
FIG. 11 is an electrical plan for motion control electronics used in the apparatus of FIG. 1.

With reference to FIG. 11, the motion control electronics is controlled by a computer 200, preferably a Windows NT Workstation, that communicates with four motor controllers 210, 214, 218, and 222 via four RS-232 communication ports. Motor controller 210 controls the motor 212 that actuates the gantry in the X-axis. Motor controller 214 controls the motor 216 that actuates the Z-axis. Motor controller 218 controls the motor 220 that actuates the first Y-axis. Motor controller 222 controls the motor 224 that actuates the second Y-axis.

The workstation 200 also communicates via a SCSI bus line 226 with a control module 228 that contains a computer, such as an Intel 386SX embedded controller. The workstation 200 performs data handling and display functions, while control module 228 only supervises data collection functions. The control module uses a relay board 230 to actuate five pneumatic valves, 232, 234, 236, 238, and 240. Pneumatic valve 232 actuates a cylinder to move the multifunctional device stage down. Pneumatic valve 234 actuates a cylinder to move the multifunctional device stage up. Pneumatic valve 236 actuates a cylinder to move the pipette plunger down. Pneumatic valve 236 is released and a spring pressure raises the plunger. Pneumatic valve 238 actuates a cylinder to move the substrate chuck up. To move the substrate chuck down, the valve 238 releases the pressure and gravity brings the substrate chuck down. Pneumatic valve 240 applies vacuum to hold the tip guide to the multifunctional device or releases the vacuum to release the tip guide. Another manual pneumatic valve, not shown, is used to actuate the vacuum that holds the microchip in the vacuum chuck.

Figure 12:
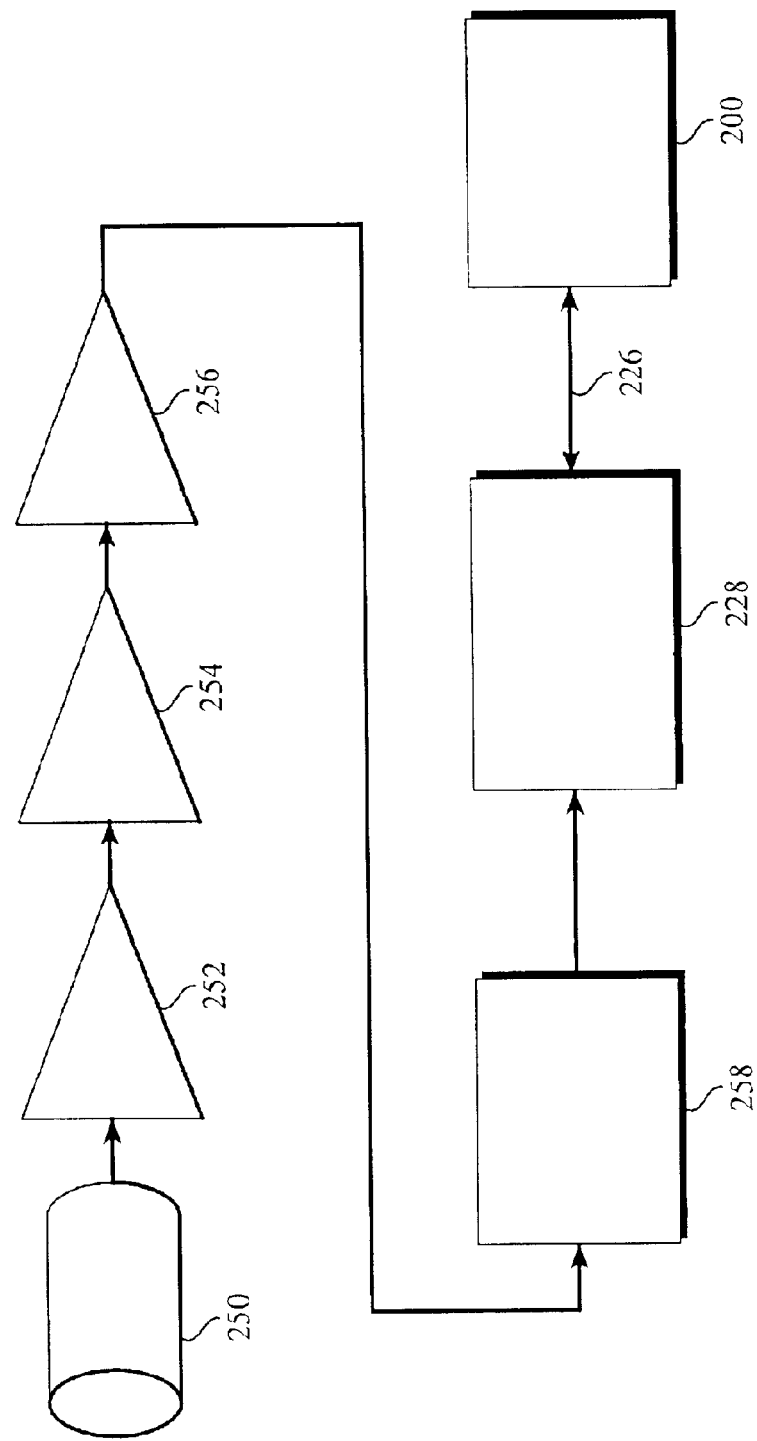
FIG. 12 is an electrical plan for data acquisition electronics used in the apparatus of FIG. 1.

FIG. 12 shows a schematic of the data acquisition electronics. The fluorescence from the sample in the microchip is first detected at a photomultiplier tube 250, such as a Hanamatsu R1477. The photomultiplier bias voltage is controlled to select the output range of the photomultiplier. The output of the photomultiplier is a current, typically in the range of 100 femtoamperes to 100 microamperes. The current is then amplified and converted to a voltage from 0.001 V to 100 V by a transimpedance amplifier 252. The output of the transimpedance amplifier is then converted by a logarithmic amplifier 254 to a logarithmic representation of the data in the range of from greater than 0 V to 10 V. The signal is then passed to a 16-bit analog-to-digital converter 256, such as a Burr-Brown ADS7805 Analog to Digital Convertor which digitizes the signal into 16 bits, giving a dynamic range of 65,536. The output of the analog-to-digital converter 256 is then processed by a digital signal processor 258, such as a Motorola 56000 Digital Signal Processor which first performs an antilogrithmic conversion, then performs a linearity correction based on an internal reference signal input into the transimpedance amplifier 252 at appropriate intervals, and finally, a square root of the signal is performed to compress the signal into 16 bits. The output of the digital signal processor 258 is sent to the aforementioned controller 228 which in turn sends the data to computer 200 via a SCSI communication line 226.

Figure 13:
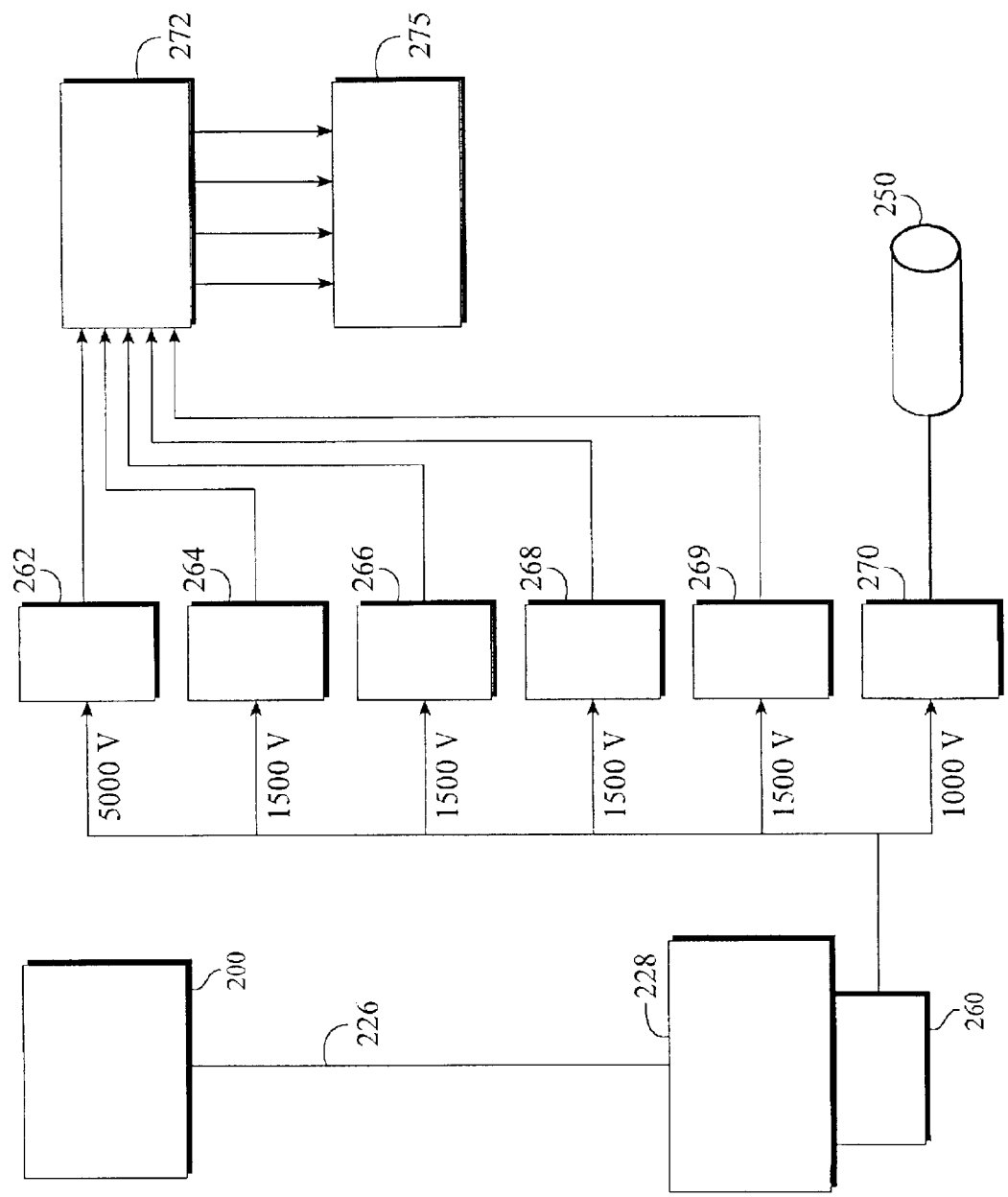
FIG. 13 is an electrical plan for high voltage control used in the apparatus of FIG. 1.

With reference to FIG. 13, the high voltage control electronics is controlled by the computer 200 that communicates with the controller 228 via the SCSI communication line 226. The control module 228 controls a digital-to-analog board 260 that contains six digital-to-analog converters. The digital-to-analog converters control the output voltages of six high voltage power supplies, 262, 264, 266, 268, 269, and 270. The high voltage power supply 270 applies the bias current to the photomultiplier tube 250. The five high voltage power supplies, 262, 264, 266, 268, and 269 are current sources that are connected to the electrode board 275 through a switching network 272. The switching network 272 contains high voltage relays that can select either ground potential as a current sink or a high voltage power supply as a current source. The high voltage power supply 262 can supply up to 5000 V in the preferred embodiment to the electrode board 275 for the anode. The other four high voltage power supplies 264, 266, 268, and 269 can supply up to 1500 V to the cathode, waste, and two sample electrodes respectively.

Figure 14:
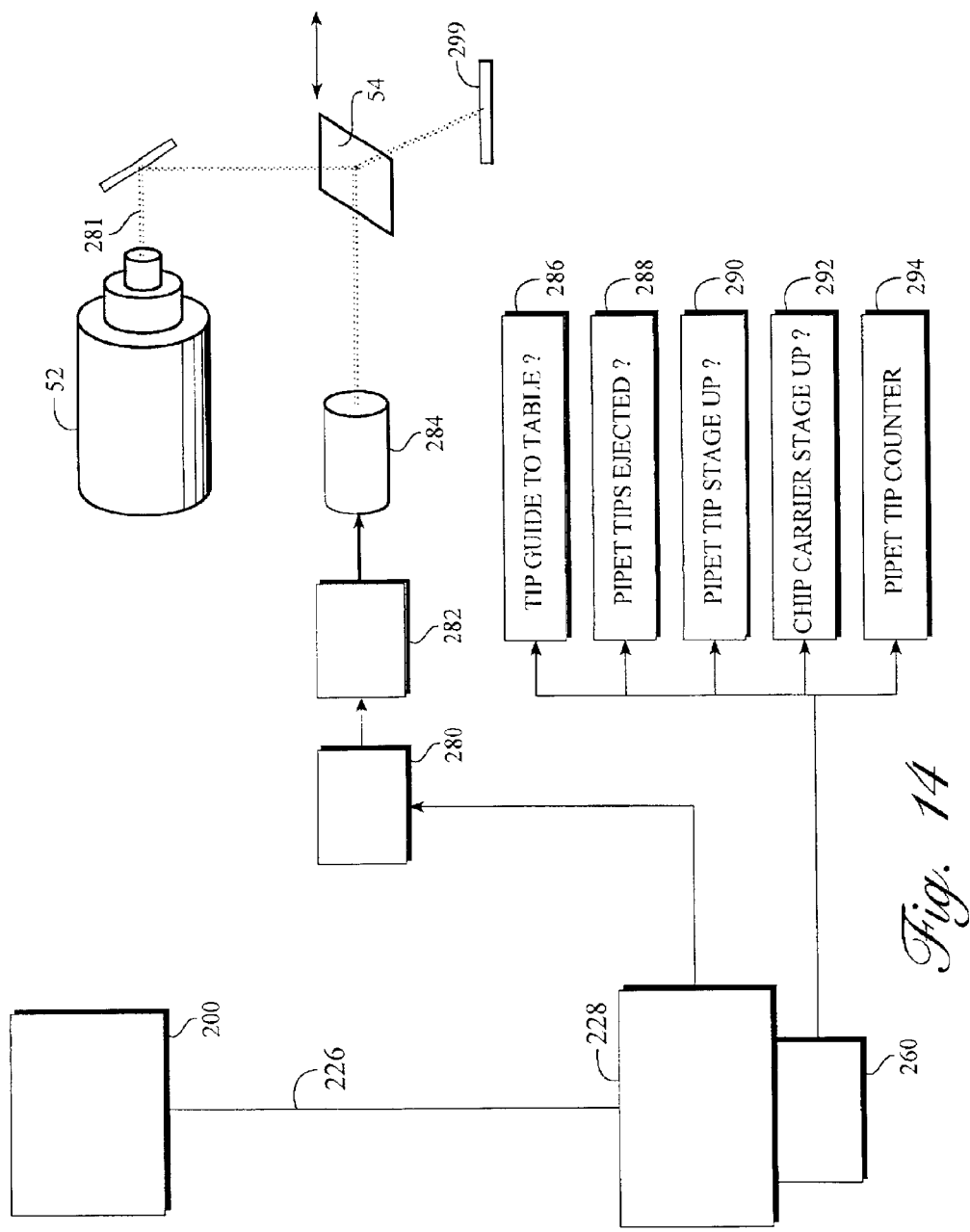
FIG. 14 is an electrical plan for sensors and an optical scanner used in the apparatus of FIG. 1.

With reference to FIG. 14, the high voltage control electronics is controlled by the computer 200 that communicates with the control module 228 via a SCSI communication line 226. The control module 228 controls a digital signal processor 280 that sends voltage pulses to a galvanometer drive board 282. The galvanometer drive board 282 sends voltages to a galvanometer 284, such as a General Scanning G325, with the scan mirror 54 mounted on it. A laser beam 281 from laser 52 is directed onto scan mirror 54. By controlling the galvanometer drive board, the position of the galvanometer can be readily adjusted to perform a line scan across the microchip 299 using beam 281. Alternative embodiments could employ a galvanometer that is controllable in two axes to scan a larger cross-sectional area or to select the optically preferred section of a microchip to scan or the use of a line generator that would illumine a line across the microchip. If a line generator were used, detection would be via a CCD device. The control module 228 controls a digital input board that receives signals from five sensors, 286, 288, 290, 292, and 294. Four of the sensors, 286, 288, 290, and 292, are single pole, single throw switches. Sensor 286 senses if the tip guide is on the table. Sensor 288 senses if the multichannel pipettor has been raised and therefore if the pipette tips have been ejected. Sensor 290 senses if the pipette stage is in the raised position. Sensor 292 senses if the microchip chuck is in the raised position. The pipette tip counter 294 is a through beam light source and detector, such as a Skan-a-matic L60/P60 series subminiature LED-IRED pair, that can sense if the beam has been interrupted. The pipette tip counter 294 is used to count the number of pipettes on the multifunctional device to verify the pickup or release of pipette tips.

The electronics, described in FIGS. 11 to 14, are controlled by software. The control software has six major functional units. The functional units are: (1) Initialize, (2) Load Samples, (3) Load Microchip, (4) Inject Samples, (5) Separate and Scan, and (6) Terminate Run. The functional units can be embodied in programming languages as modules, subroutines, objects, scripts, or other organizations.

The Initialize functional unit prepares the system by initializing the electronics, the stages, the multifunctional device, and the Y-stages. The initialization is comprised of initializing the electronics, homing the stages, initializing the multifunctional device by ejecting any pipette tips and preparing any liquid or microfluidic subsystems, and moving the stages to prepare for sample loading.

The Load Samples functional unit loads samples from reservoirs such as microtiter plates into the microchip. The software controls processing for each plate. The samples from a plate can be looped through by sets of wells that can be simultaneously transferred by the multifunctional device. New pipette tips and the tip guide are picked up. The samples are then loaded into the pipettors from the plates. The multifunctional device is moved to the microchip. At the microchip, the samples are deposited into the sample loading wells. The sets of wells in the plate are then looped through until the microchip has been completely loaded. If the microchip has not been completely loaded, the remaining wells are noted. The sets of wells loaded can be rows, columns, or separated wells. In another embodiment, all the samples might be loaded at once by a simultaneous loading by a device, such as a capillary loader, or from another microchip containing samples, from a piezo electric device with multiple channels, or by other loading strategies.

The Load Microchip functional unit initializes stages as required, moves the loaded microchip into position at the scanner, and docks the microchip at a position in the focal plane of the detector if an optical detection system is employed.

The Inject Samples functional unit is designed to move the samples from the sample loading ports into the injection region of the microchip. The Inject Samples functional unit sets and executes an injection profile that controls the high voltage power to each electrode. A profile specifies the electrode, the voltage potential, and the time for each potential. Simple or complex injection and separation profiles may be employed. In other embodiments, pressure, capillary flow, magnetic fields, or other means can be employed as a profile to move the samples from the sample loading ports into an injector.

The Separate and Scan functional unit performs all functions to separate the injected samples into constituent components for analysis and detection of the components. The high voltage power supplies are first set to the separation profiles. The file name for the data is selected and the data file created. The data acquisition electronics are diagnosed, calibrated, and parameters set; the parameters may include the number of pixels per line, the number of lines, the timing for the data acquisition electronics, or other information. The photomultiplier tube bias voltage is set. There may be multiple photomultiplier tubes as well. The galvanometer is started. The separation profiles are then initiated and voltages applied to the electrodes. The scan is initiated and all the data packets read until the scan parameters have been accomplished. The galvanometer is then stopped, and the voltage to the photomultiplier tube and the power supplies reset to zero or other potentials.

In the Terminate Run functional unit, the stages are initialized as required and then the wash tray is moved under the electrodes. They are then cleaned by moving the wash tray up and down with a pause while the electrodes are immersed in the cleaning solution, which can be water, or have additional components. Alternative embodiments are washing the electrodes with one or a series of liquids or gases or cleaning of the electrodes by heating, plasma treatment, microwave, or other methods to clean the electrodes.

After the Terminate Run functional unit has been executed, the system is ready for another cycle. If another microchip is to be used, the system may start with the Initialization functional unit. Alternatively, if multiple samples are multiplexed into each separation channel, the software might continue at the Inject Samples functional unit, followed by the Separate and Scan, and the Terminate Run functional units.

In the embodiment described above, parallel, spaced apart linear tracks, together with a transverse gantry, were shown to provide the necessary robotic motion to accomplish tasks of loading microchannels with sample and conducting chemical testing and analysis. It is not necessary that a linear format be used.

Figure 15:
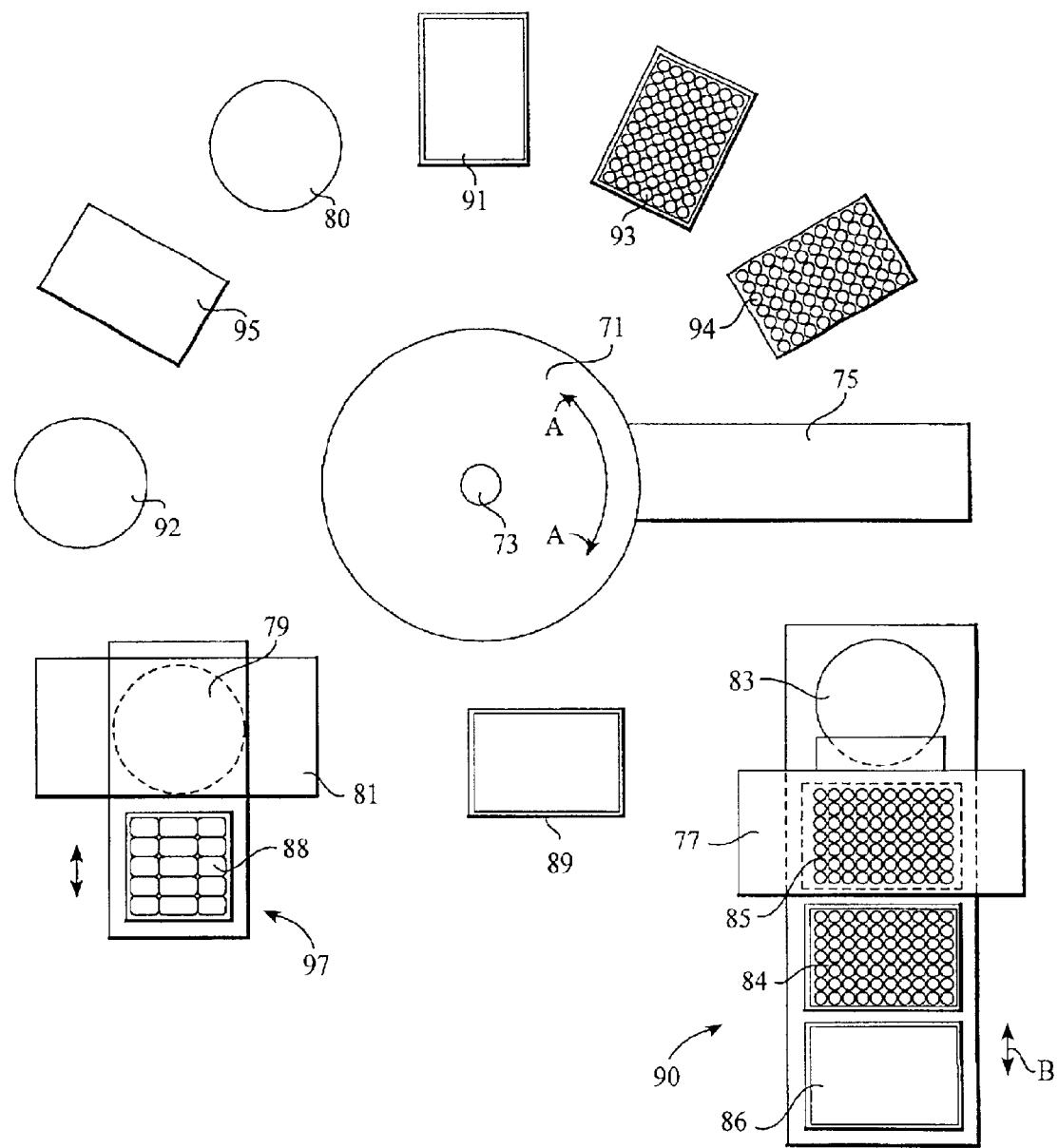
FIG. 15 is a plan view of an alternate embodiment of the apparatus of automatic handling and presentation of specimens into the microchip.

FIG. 15 shows a rotational format in which a transfer arm robot 71 rotates about a central axis 73, rotating in either direction indicated by arrowheads A. The transfer arm 71 carries a gripper arm 75 having a tool for picking up microchips from new microchip stack 80, as well as a cassette pickup tool for picking cassettes of samples from sample stack 94, new tip cassettes from new tip stack 93, used tip cassettes from used tip stack 91 and wash or other cassettes from stack 95. The transfer arm 71 can swing over a plurality of radially disposed storage locations where these cassettes are stored and move them to loading station 90 which has a linear track allowing motion in reciprocal directions indicated by the arrow B.

Figure 16:
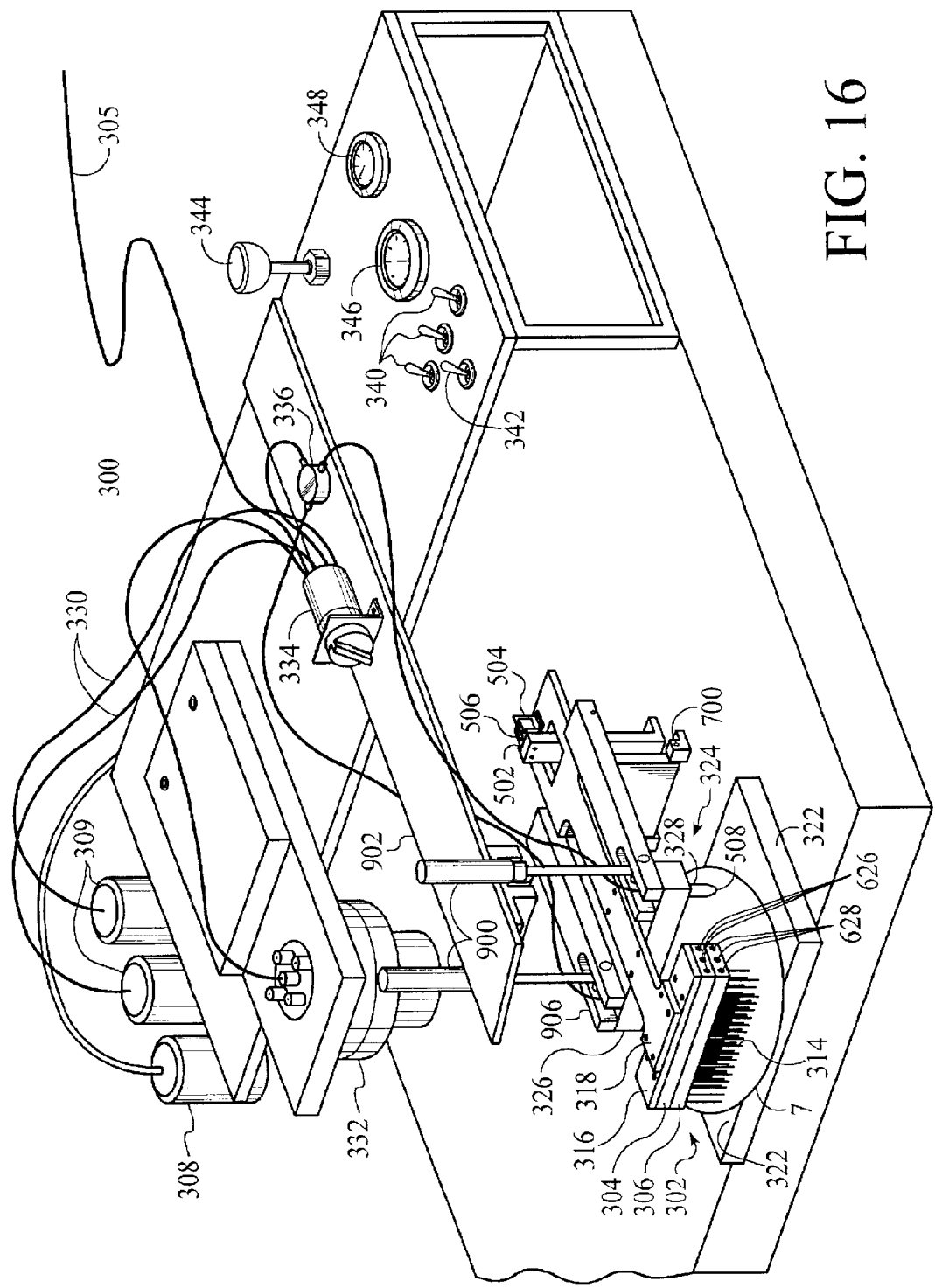
FIG. 16 is a perspective view of the apparatus for filling and cleaning wells and channels of a microchip substrate featuring a manifold without vacuum supply tubes, pressure tubes and a vacuum source in accordance with the present invention.

The transfer arm robot 71, pictured in FIG. 15, is also able to transfer microchips between various different locations and a microchip wash station 89 comprising an apparatus for cleaning and filling channels and inlet ports of the microchip substrate (FIG. 16). In one embodiment, the apparatus is positioned next to analysis station 97 (FIG. 15). A means for moving microchip substrates, such as gripper arm 75, is incorporated. In one embodiment, such means comprises a device able to hold two microchips and capable of rotating them back and forth between each station. This movement can be performed by linear motion.

Loading station 90 comprising a first frame is spanned by a gantry 77 that mounts a multifunctional tool containing a ganged pipettor capable of up and down motion. New tips are first picked up by the multifunctional tool carried on gantry 77 out of tip rack 84. This requires that the loading station 90 advance the tip rack 84 under gantry 77 so that the ganged pipettor supported on the multifunctional device on the gantry 77 can reach the new tips and push them onto the pipettor. The pipettor is raised and the sample rack 85 is placed below the gantry so that pipettor can move down and pick up desired quantities of sample. Next the microchip at microchip station 83 is moved below the gantry 77 and samples are placed into the holes in the microchip in the manner previously described. The loading sequence is repeated until all microchip wells have been loaded with sample.

Once the microchip at microchip station 83 has been loaded with sample, the gripper arm 75 moves the microchip to the analysis station 97 comprising a second frame where a scanner is supported by platform 81. Thereafter, the gripper arm picks another microchip off of the stack at the microchip stack 80 and moves it to the microchip station 83 for further processing.

The analysis station 97 can simultaneously analyze a microchip while another is being loaded at the loading station 90 or cleaned at the wash station 89. The analysis station 97 also supports electrodes that are inserted into vias or apertures in the microchip which make contact with the liquid in the microchannels for stimulating sample injection and separation as previously described. The appropriate voltages are applied for sample injection and then to stimulate electrophoretic separation while scanning by the scanner, preferable a scanning confocal microscope. When data collection is complete, the stage is moved to position the wash wells 88 beneath the scanner so that the electrodes may be cleaned by rinsing in the wash wells prior to further use and the gripper arm 75 can move the microchip to the used microchip stack 92 or to the wash station 89 comprising the apparatus for cleaning and filling inlet ports and channels of a microchip substrate. With this system, a malfunctioning microchip may be discarded in used microchip stack 92 and replaced automatically from new microchip stack 80 for uninterrupted operation. Electronics and control software would be similar to that described above.

FIG. 16 shows an apparatus 300 for cleaning and filling inlet ports and channels of a microchip/analytical substrate 7. The apparatus features a manifold 302 with an upper chamber 304 and a lower chamber 306, a tube-in tube assembly 314 and a pressure injector 324. Solutions travel from a container 308 through tubing 310 (FIG. 21) into the upper chamber 304 of the manifold 302. From the manifold the solutions flow through the tube-in-tube assembly 314 to the microchip inlet ports and channels, for cleaning of the inlet ports and channels. Simultaneously, a vacuum source connected to the lower chamber 306 of manifold 302 through tubing 312 (FIG. 21) provides suction for removing solutions from the inlet ports and channels. Additionally, the pressure injector 324 introduces pressurized solutions such as matrix or wash into common openings of the microchip 7 which lead to microchannels and inlet ports. The pressurized solutions are used to clean and/or prepare the microchannels for use.

Figure 17:
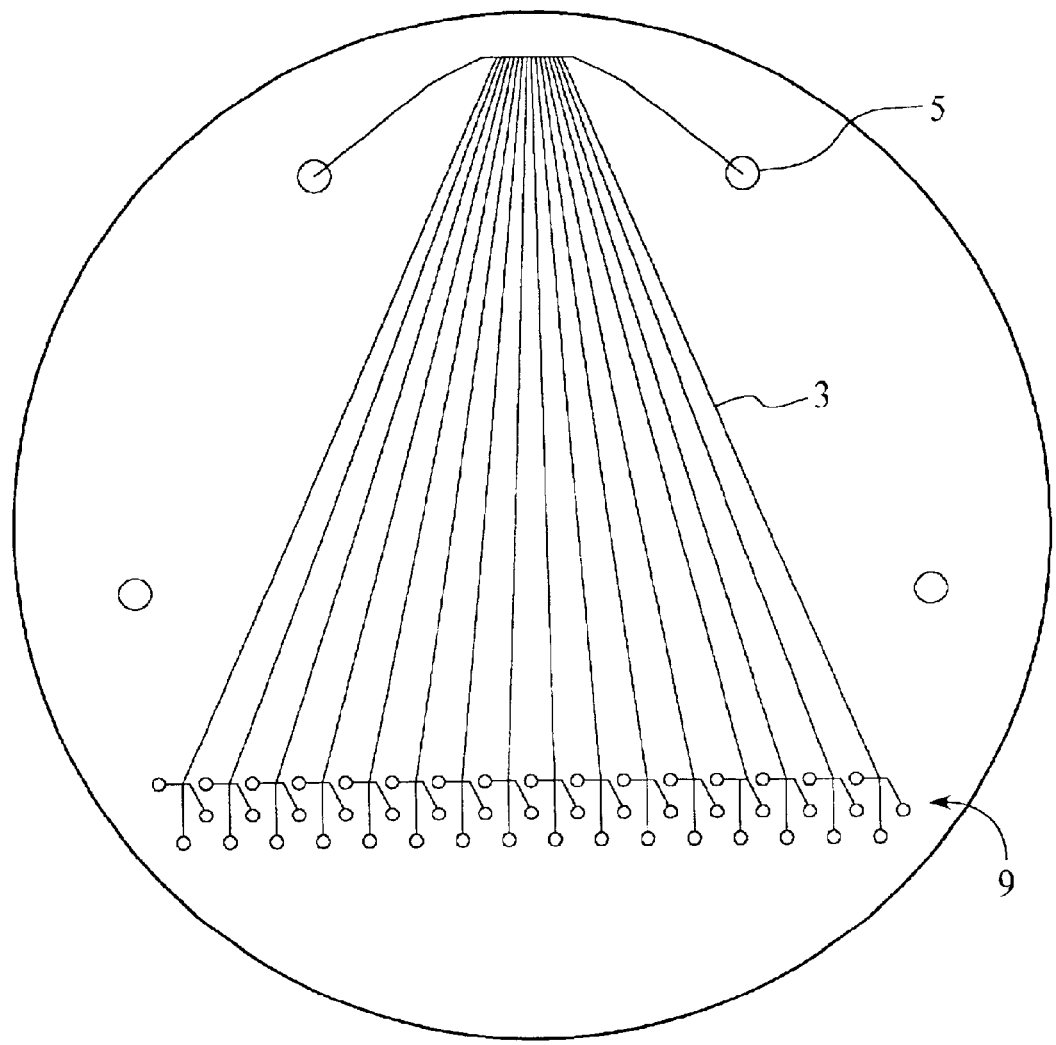
FIG. 17 is a plan view of a microchip substrate used in conjunction with the apparatus of FIG. 16.

With reference to FIG. 17, there is seen an example of a microchip 7 that is used in conjunction with the apparatus 300. The microchip 7 has 16 microchannels 3, 48 inlet ports or openings 9 (including cathodes, sample ports and waste ports) at one end and two anodes or openings 5 at a second end. The microchip is placed upon the platform 322 pictured in the apparatus 300 of FIG. 16.

Referring back to FIG. 16, it is seen that the tube-in-tube assembly 314 extends from the manifold 302 to enter the inlet ports 9 of the microchip substrate 7, forming a rectangular array of three rows and sixteen columns as shown in FIG. 16 to correspond to the number and spacing of the inlet ports of the microchip used. In another embodiment, the apparatus may be modified accordingly so that the array which extends from the manifold can correspond to any number and spacing of inlet ports of the microchip 7. In one embodiment the assembly 314 is comprised of hyperdermic stock, stainless steel tubing. However, other materials which prevent corrosion may also be used.

In FIG. 16 there is featured, to the rear of manifold 302 a pressure injector 324 mounted to arm 318. The pressure injector 324 includes a block 326 containing two pressure tip injectors 328 each within one of two openings within the pressure injector block 326. In alternate embodiments there may be one or more pressure tip injectors 328. The pressure tip injectors 328 are made from Teflon. Teflon is desirable so that the pressure tip injectors may easily slide within the openings of the pressure tip manifold 326. In the alternative, stainless steel, polysulphone, or other materials reasonably resistant to corrosion may be used.

The pressure injector 324 is used to inject solution into at least one common hollow opening or anode port 5 of the microchip substrate 7 (FIG. 17) which provide a common opening to microchannels 3 of the microchip substrate.

With reference to FIGS. 18(a) and 18(b) the tube-in-tube assembly 314 and the openings within which it is contained are pictured in detail. Tube-in-tube assembly 314 is contained within upper 304 and lower chamber 306 manifold surface openings that align with the inlet ports on the microchip substrate. The tube-in-tube assembly also aligns with the inlet ports 9 on the microchip substrate 7. In one embodiment, the number of openings per each surface of the upper 304 and lower 306 chambers of the manifold 302 is equal to the number of inlet ports 9 present on the microchip substrate 7 and the spacings between the openings corresponds to the spacings between the inlet ports 9 so that the openings align with the inlet ports.

In FIGS. 18(a) and (b) it is seen that the tube-in-tube assembly has an array of pressure tubes 606 each contained within a larger vacuum tube 608 contained within openings.

In this embodiment, the pressure tubes 606 of tube-in-tube assembly 314 are fabricated from 25-gauge regular wall stainless steel tubing and the vacuum tubes 608 are fabricated from 19 gauge thin wall tubes. However, other sizes and types of tubing may be used.

The vacuum tube 608 surrounds the pressure tube 606 beginning at an opening 634 of a lower surface 624 of the lower chamber 306 and continues to surround the pressure tube 606 as the tube-in-tube assembly 314 extends from the manifold 302 to enter the inlet ports 9 of the microchip substrate 7. Each tube-in-tube assembly pressure tube 606 is found within one of a plurality of openings 630 (FIG. 18(b)) of a lower surface 620 of the upper chamber 304, and within openings 634 of the lower surface 624 of the lower chamber 306. Each tube-in-tube assembly vacuum tube 608 surrounding the pressure tube 606 is found within one of a plurality of openings 634 of the lower surface 624 of the lower chamber 306 which are larger than the openings 630.

As shown in FIG. 18(b) openings are machined within the lower surface 620 of the upper chamber 304, and the lower surface 624 of the lower chamber 306 of the manifold 302. The manifold 302 in one embodiment comprises a stainless steel material to avoid corrosion. A gasket is used to seal the upper and lower chambers of the manifold.

Seen in FIGS. 18(a) and (b) are two front compartments, an upper 410 and lower 416, of the manifold 302 sharing a row of the tube-in-tube assembly 314. The upper chamber 304 has at least one upper compartment and the lower chamber 306 has at least one lower compartment. Preferably, there are six compartments (FIGS. 19 and 20), three groups of one upper and one lower compartment, each group of upper and lower compartments sharing a row of tubes that extend from the entire manifold 302 forming an array of three rows corresponding to the spacing and number of inlet ports 9 of the microchip 7.

Figure 19:
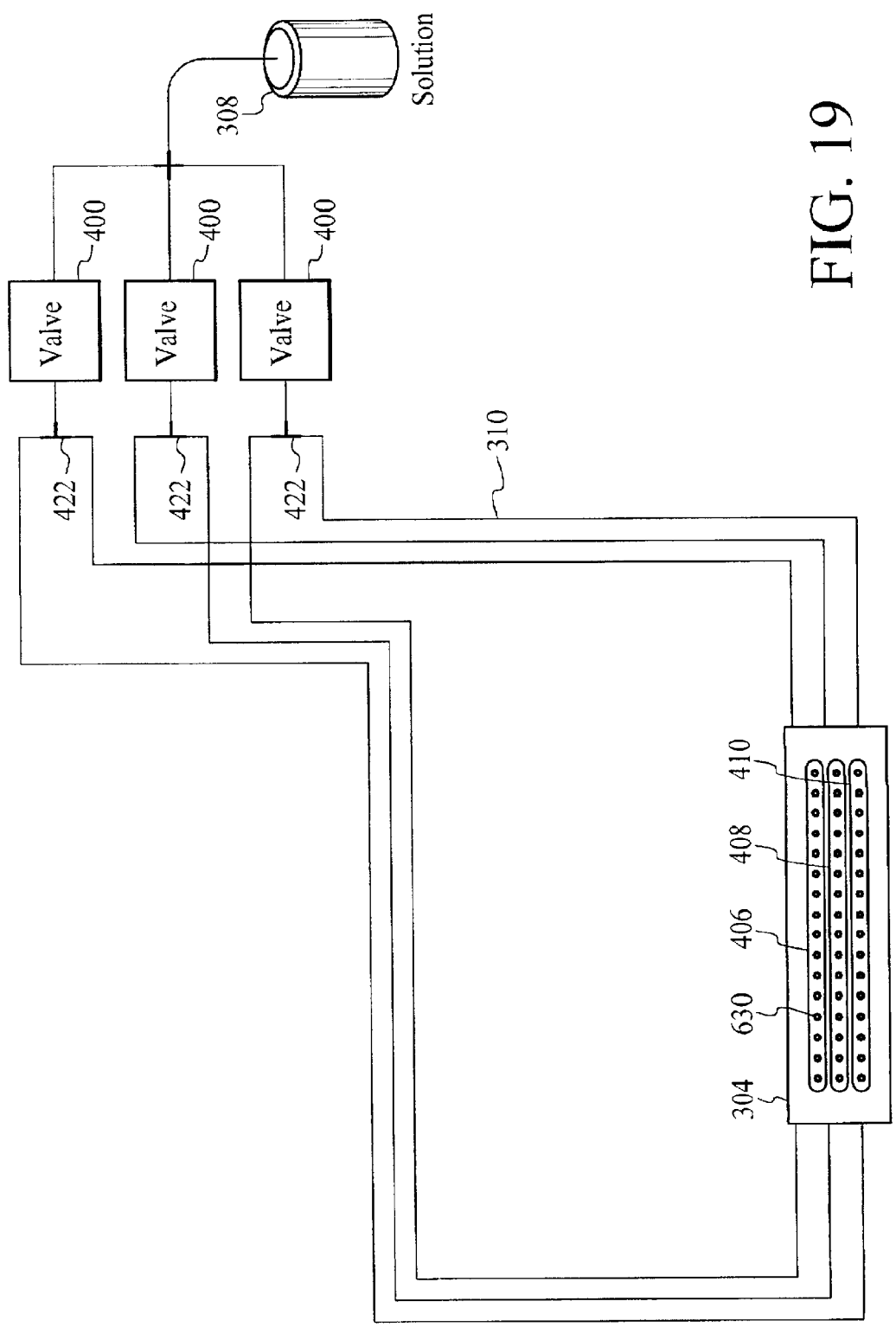
FIG. 19 is a plan view of an upper chamber of the manifold of the apparatus of FIG. 16 connected to a container of solution.
Figure 20:
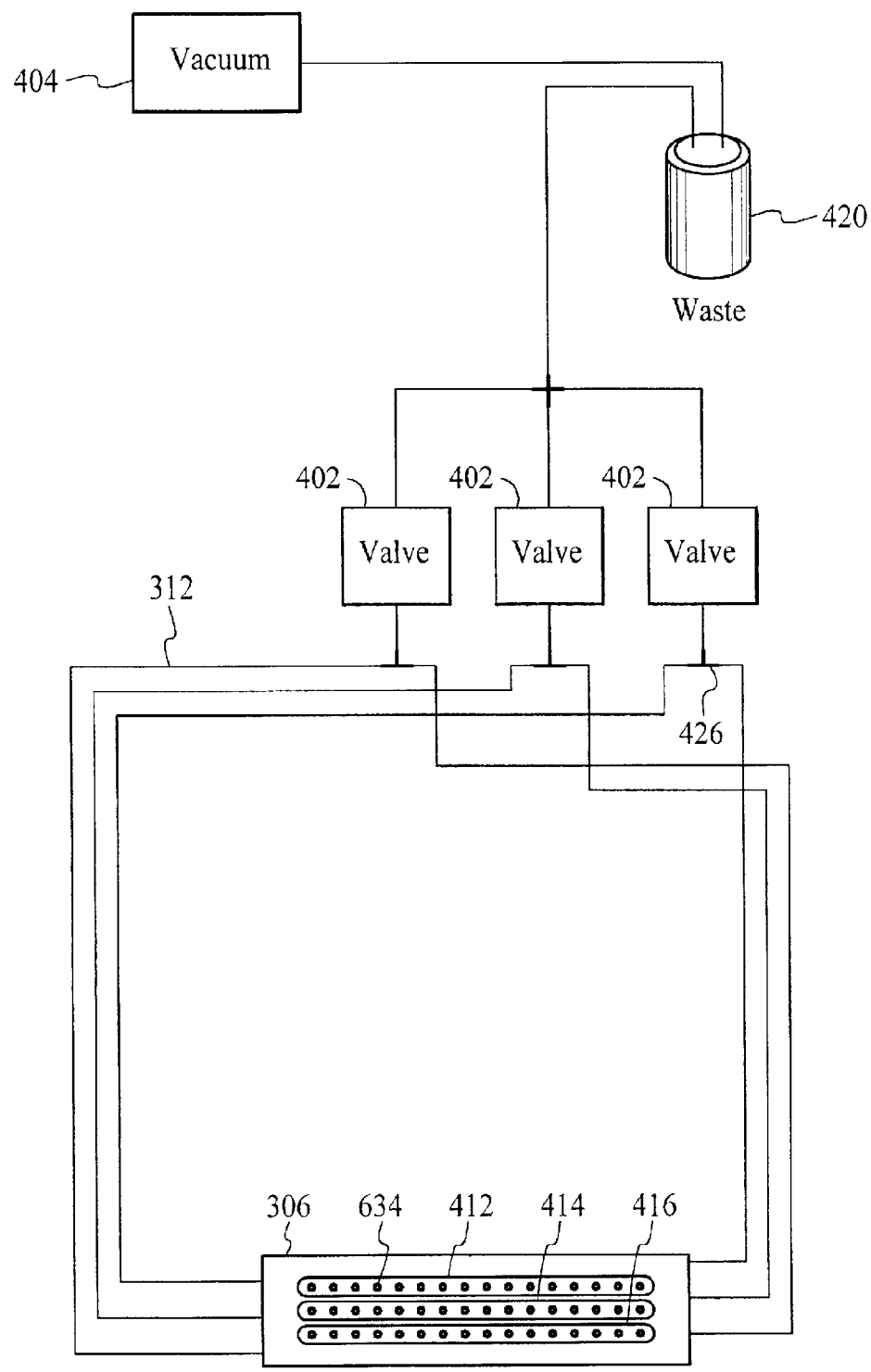
FIG. 20 is a plan view of a lower chamber of the manifold of the apparatus of FIG. 16 connected to a vacuum source.

A detailed description of the internal structure of the manifold 302 including its compartments will now be provided. With reference to FIGS. 19 and 20, it is seen that each chamber, 304 and 306, of the manifold 302 may be internally divided into compartments. In one embodiment the upper chamber 304 is separated into three compartments 406, 408 and 410 and the lower chamber 306 is also separated into three compartments 412, 414 and 416. The lower chamber 306 is directly beneath the upper chamber 304 and the compartments of the upper and lower manifold chambers align.

With reference to FIG. 19, the upper chamber 304 of manifold 302 provides a passage between one or more containers of solution 308 to inlet ports 9 of the microchip substrate 7 (FIG. 17). In one embodiment, each side of the upper chamber 304 of the manifold 302 has three openings 626 (FIG. 16), one for each side of each compartment. The number of openings varies with the number of compartments present. In another embodiment only one side of a compartment has an opening. There is seen within each side opening pressure supply tubing 310 which connects the upper chamber 304 of the manifold 302 to the container of solution 308. In one embodiment the fittings used to connect the pressure supply tubing 310 are sized such that they do not restrict the flow of solution to the pressure tubes of the tube-in-tube assembly 314.

Shown in this embodiment is one container of solution 308. However, in other embodiments any number of containers of solution may be used. The containers contain solutions such as water or wash used for cleaning the inlet ports of the microchip substrates for use in molecular separation and chemical analysis of samples. The containers may also contain filters for the solutions.

In FIG. 19, three pressure valves 400 are shown. One side of each valve is connected through a tee fitting 422 to pressure supply tubing 310 and then to each of the two fittings (not shown) on the upper chamber 304 of manifold 302 corresponding to one compartment; 410 front, 408 middle, 406 rear. The other side of each valve is connected to a container of solution 308.

With reference to FIG. 20, it is seen that the lower chamber 306 of the manifold 302 provides a passage from a vacuum source 404 to inlet ports 9 of the microchip substrate 7. Preferably, each side of the lower chamber of the manifold has three openings 628 (FIG. 16) or one for each side of each compartment, for a total of six. The number of openings varies with the number of compartments present. In one embodiment only one side of a compartment has an opening. Within each side opening is seen vacuum supply tubing 312 which connects the lower chamber 306 of the manifold 302 to the vacuum source 404.

In FIG. 20, it is seen that the vacuum supply tubes 312 are present in an arrangement similar to that of the pressure tubes 310. Seen in FIG. 20 are three vacuum valves 402 that connect vacuum supply tubes 312 that extend from the front 416, middle 414 and rear 412 compartments of the lower chamber 306 in three groups of two. One side of each vacuum valve is connected through a tee fitting 426 to vacuum supply tubing 312 and then to each of the two fittings (not shown) on the lower chamber 306 of manifold 302 corresponding to one compartment; 416 front, 414 middle, 412 rear. The other side of each vacuum valve is connected to the vacuum source 404 through a waste collection container 420.

It should be noted that embodiments of the pressure 310 and vacuum supply tubes 312 arrangements other than the one depicted are possible and that the invention is not intended to be limited to the embodiment described here.

A detailed description of how the pressure injector 324 is connected to a reservoir of solution and/or a line of air or nitrogen will now be provided. Referring back to FIG. 16, within each pressure tip injector 328 is tubing 330 connected to a reservoir of solution 332 or to containers of solution 309. The tubing defines a passage for solution from the reservoir of high pressure solution or from a container of solution to a stream selector valve 334.

The stream selector valve 334 enables air or nitrogen from line 305 to be routed to the chip 7, pictured in FIG. 16. It also enables a particular solution to be selected from reservoirs 332 or containers 309. A specific tube 330 containing a specific solution may be selected with the stream selector valve 334 which activates the passage of the solution within the selected tube. The stream selector valve 334 may also be placed in the off position resulting in no selection of solution.

From the reservoir of solution 332 or the containers of solution 309 the tubing 330 may pass through a filter to filter the selected solution contained within the tubing. If prefiltered matrix or other solution is selected to pass from the reservoir 332 through the tubing 330 a filter is not necessary. In one embodiment containers 309 have filters.

From the stream selector valve 334, the tubing enters a T apparatus 336 where the tubing 330, and the solution contained within is split in two directions and enters each of the pressure tip injectors 328 arranged within the openings of the pressure injector block 326.

Referring again to FIG. 16 and to the manifold 302, it is seen that the manifold has a lid 316 which is bolted to the upper chamber 304 of the manifold 302. The manifold 302 is mounted on an arm 318 that is secured to the lid 316.

Figure 21:
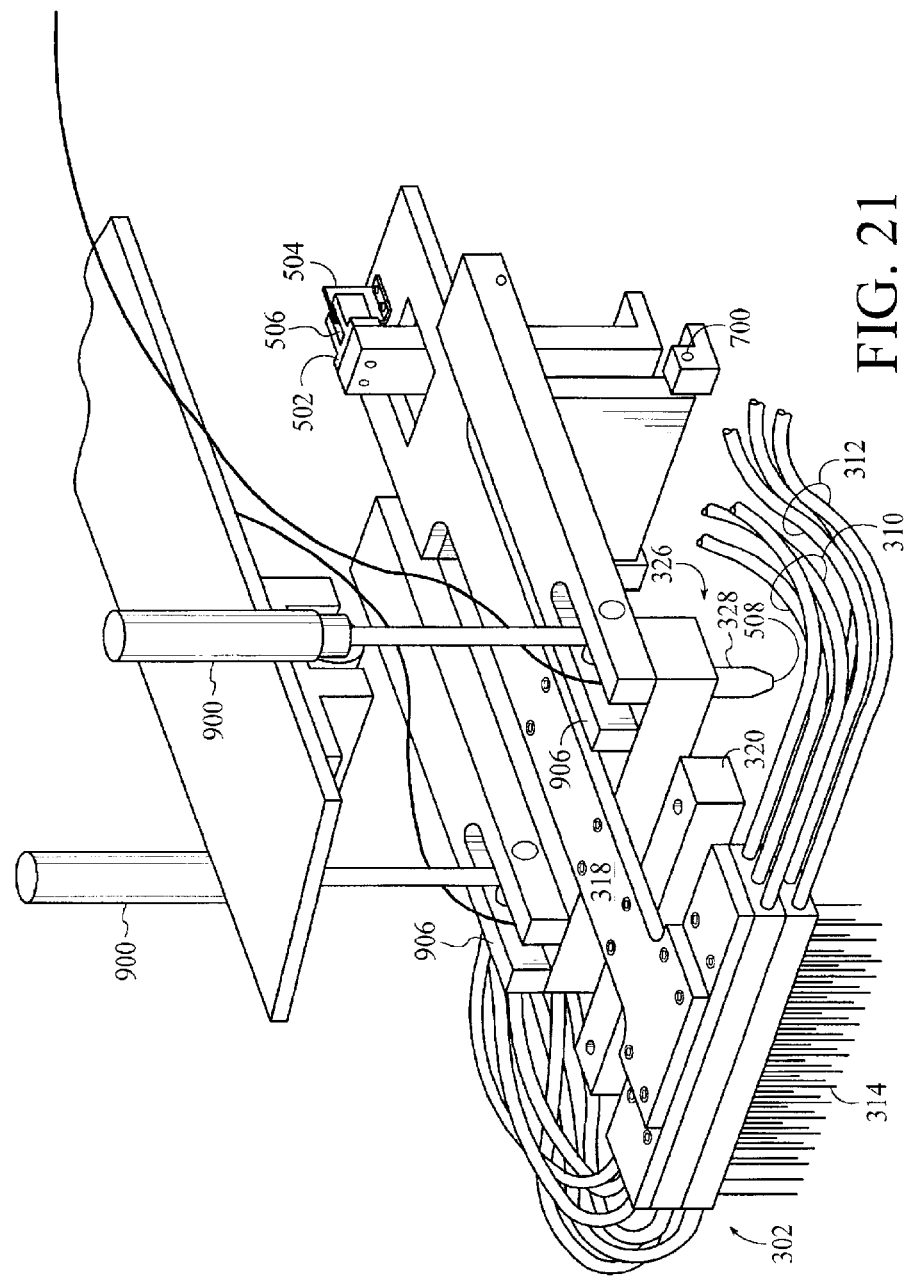
FIG. 21 is a perspective view of the manifold, alignment block, pressure tip injectors, optical interrupter sensor assembly, dual acting cylinders and respective arms of the apparatus of FIG. 16.

In one embodiment, also mounted on the arm 318 is an alignment block 320, pictured in FIG. 21. The alignment block 320 is located to the rear of the manifold 302 comprising alignment pins (not shown) used to align the microchip substrate 7 with the tube-in-tube assembly 314 of the manifold 302. Alignment openings (not shown) that go part way through the microchip are present on an upper surface of the microchip substrate. When the alignment pins of the block engage the alignment openings on the microchip 7, the microchip substrate is aligned to the tube-in-tube assembly 314 of the apparatus 300. In an alternative embodiment the alignment pins (not shown) are present on a platform 322 upon which the microchip substrate is placed.

Referring back to FIG. 16, there are pictured individual switches 340. Switches 340 are used to select the function of the individual groups of pressure supply tubes 310 and vacuum supply tubes 312. Each switch corresponds to pressure supply tubes and vacuum supply tubes present in the front, middle, or rear openings of the compartments of the manifold 302. In the upper position shown in FIG. 16, the pressure and vacuum supply tubes are activated in all three groups. A switch in the middle position indicates that a group of vacuum and pressure supply tubes are inactive. A switch in the down position indicates that only the vacuum supply tubes 312 are active. For convenience, a master switch 342 may be used to control the function of all three groups of tubes and to partially override the settings of individual switches 340 unless any of switches 340 is in the off position in which case that group is always off.

The master switch position shown in FIG. 16 indicates the pressure supply tubes 310 and vacuum supply tubes 312 are activated if the individual switches 340 are in the up position. If the switch 342 is moved to the middle position, all three groups of tubes will be inactivated. If the switch 342 is moved to the down position, all three groups of vacuum supply tubes 310 only will be activated as long as individual switches 340 are in either an up or down position. This master switch override function allows a final vacuuming step even if an individual switch 340 is set for both a pressure and vacuum function. During operation of the apparatus 300, all of the inlet ports 9 are washed and vacuumed at the same time and then all of the inlet ports 9 are vacuumed towards the end of the operation. The master switch 342 overrides the individual switches, so rather than operating all of the switches 340 individually where the groups of supply tubes are doing the same function, a master switch 342 is conveniently used.

In FIG. 16 a low pressure regulator 344, vacuum gauge 346 and pressure gauge 348 are shown. The fluid pressures are established for the various containers of solution contained within pressurized refillable containers 308 with the low pressure regulator 344 as required for their respective function. The vacuum gauge 346 and pressure gauge 348 indicate the pressure of the vacuum and the pressure supply tubes, respectively. High pressure solutions are similarly regulated with external regulators (not shown). Pressure release valves (not shown) are incorporated to vent the fluid containers for refilling.

A user may direct operation of the apparatus using the switches. Alternatively the whole wash and fill operation may be computerized in which case the switches would not be necessary. A computer is also used for controlling the apparatus for the automatic handling and introduction/injection of specimens into the microchips for parallel high throughput analysis in microchannels as described above. Therefore, all of the functions may be controlled with the same computer and the apparatus for cleaning and filling channels and inlet ports of the microchip substrate may be integrated with the apparatus for automatic handling and presentation of specimens into the microchips.

The operation of the apparatus will now be described. In use, the microchip substrate 7 (FIG. 17) such as one that has been used in the molecular separation and chemical analysis of samples, or one that lacks separation media such as matrix in its microchannels, is placed upon the platform 322 (FIG. 16) where pins in the alignment block 320 (FIG. 21) of the arm 318 engage alignment holes (not shown) present on the microchip substrate 7. In an alternate embodiment, the microchip substrate has alignment holes located on or accessible through a bottom surface of the microchip. These holes engage pins protruding above the upper surface of platform 322 for alignment of the microchip substrate.

Figure 22A:
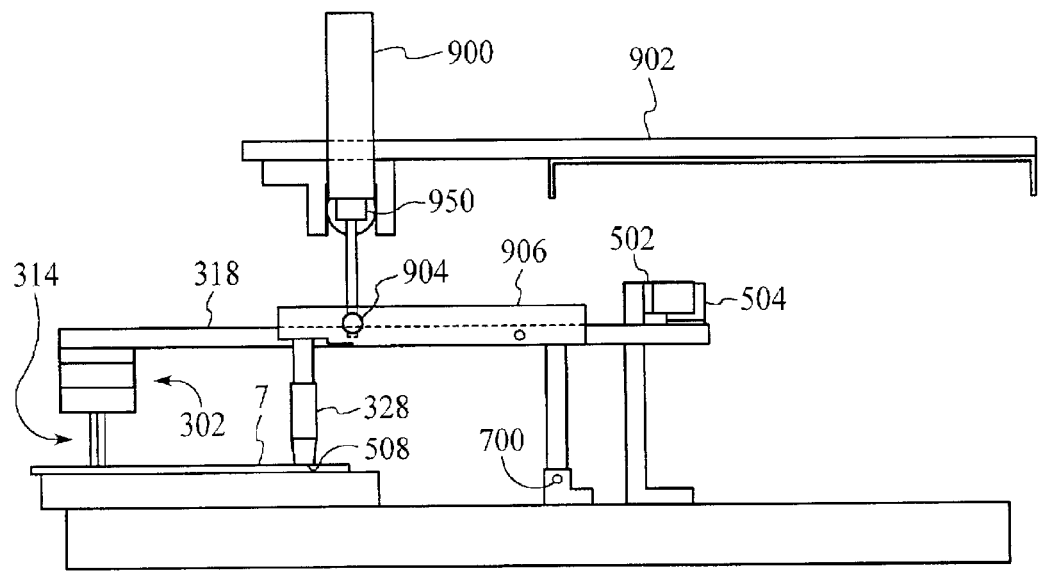
FIGS. 22(a) and 22(b) are a plan view of the apparatus shown in FIG. 16.
Figure 22B:
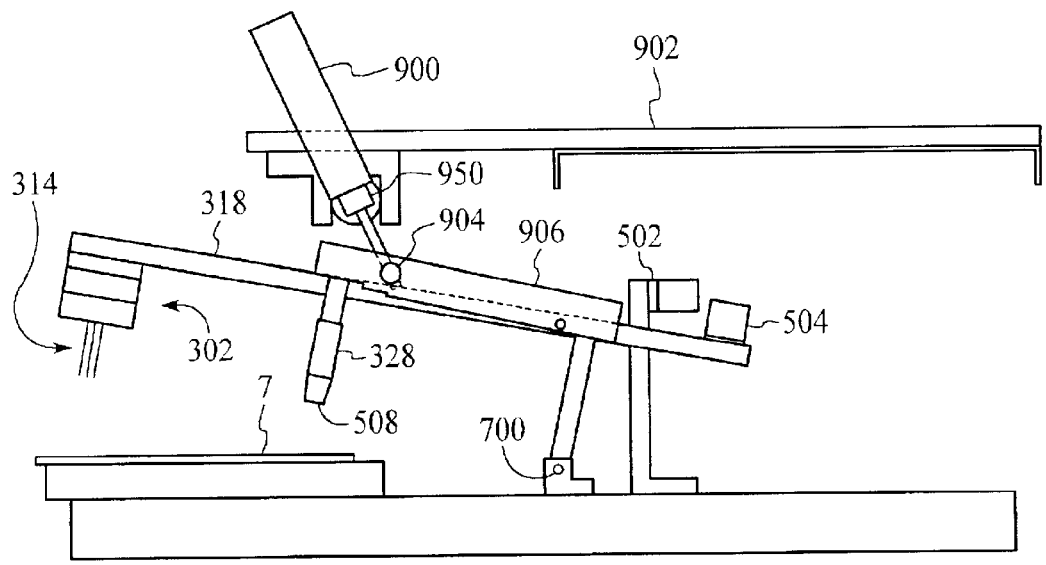

FIG. 22(a) and FIG. 22(b) show one of the dual acting cylinders 900, which raise and lower the arm 318 and also actuate arms 906, in greater detail. Adjustable stops are incorporated for up and down positioning of arm 318. The arm has a rear pivot 700 that allows the tube-in-tube assembly 314 and the pressure tip injectors 328 to be lowered so as to engage the inlet ports 9 and the anode ports 5 of the microchip substrate 7, respectively, as shown in FIG. 22(a). Connected to arms 906 are dual acting air cylinders 900 that actuate the arm 318 and arms 906. A fixed support 902 supports each air cylinder 900. Each cylinder 900 pivots at points 904 and 950.

FIG. 22(b) shows the tube-in-tube assembly 314 and pressure tip injectors 328 before they have engaged the inlet ports 9 and the anode ports 5, respectively. Precision positioning is required as the outer tubes of the tube-in-tube assembly 314 are only slightly smaller in diameter than the inlet port openings 9. The arm pivot 700 is located at a point on a plane established by the top surface of the microchip 7 such that there is minimal lateral translation of the tube-in-tube assembly 314 relative to the inlet ports 9 at the time of engagement of the tube-in-tube assembly 314 with the inlet ports 9.

Seen in FIG. 22(a) and FIG. 22(b), is a flag 504 attached to arm 318 as part of an optical interrupter sensor assembly. This assembly is incorporated to sense tube-in-tube assembly 314 engagement with the microchip 7. The sensor 502 is mounted in a stationary position while the flag 504 moves with arm 318. When the tube-in-tube assembly engages microchip substrate 7, the flag 504 interrupts a beam of light (not shown) that passes through the slot 506 (FIG. 21) in the sensor 502 and causes the sensor output to change logic states.

Two different pressures are used when the arm 318 is lowered. With reference to FIG. 22(a), the pressure applied to air cylinders 900 is routed through a solenoid valve (not shown) controlled by the logic state of the optical interrupter sensor 502. Each pressure tip injector 328 is coupled to a separate air cylinder 900, mounted to a fixed support 902. Each air cylinder 900 is connected to an actuator arm 906. The actuator arms 906 contact the upper ends of the pressure tip injectors and insure that mainly axial forces are applied to the pressure tip injectors 328 while allowing arm 318 free motion. The arm 318 is first lowered with low pressure and low force, approximately 5–10 PSI. This minimal pressure applied to air cylinders 900 results in a force of about 0.5 pounds applied to arm 318 (at the tube-in-tube assembly end) as the tube-in-tube assembly 314 engages the inlet ports 9. This low pressure is not great enough to overcome the return spring force of pressure tip injectors 328 return springs, therefore when the arm is first lowered, the pressure tip injectors do not come into contact with the anode ports 5. However, it is sufficient to lower arm 318 so that the tube-in-tube assembly 314 engages all of the inlet ports 9 of the microchip substrate 7.

Once the arm 318 has lowered far enough for the tube-in-tube assembly 314 to engage the ports 9 of the microchip substrate 7 and the flag 504 interrupts the light path of the sensor 502, the solenoid valve is actuated and high pressure is routed to air cylinders 900. This high pressure is great enough to overcome the return spring force of the pressure tip injectors 328 which are in turn lowered to engage the common anode ports 5 (FIG. 17) with sufficiently high force to maintain a high-pressure seal. When the tube-in-tube assembly 314 engages the microchip substrate 7, the pressure to cylinders 900 is increased 5–20 fold so that the pressure tips are lowered into contact with the top surface of the microchip with sufficient force to compress the o-rings 508 located at the bottom of each of the pressure tip injectors 328 and form a seal with the common anode ports 5 on the microchip 7 (FIG. 20(a)). This higher pressure, applied to air cylinders 900, is in the range of 50–100 PSI. A travel stop (not shown) prevents over travel of the tube-in-tube assembly 314.

The pressure tip injectors 328, designed to seal against the top surface of the microchip substrate 7, contact the microchip substrate with a fair amount of force after the tube-in-tube assembly 314 has engaged the inlet ports 9. The pressure tip injectors 328 can move up and down in the pressure injector block 326 independently of arm 318 once the pressure tip injector return spring force has been exceeded. This allows the tube-in-tube assembly 314 to engage the microchip 7 gently while the pressure tip injectors 328 are maintained in a retracted position by the return springs until high pressure is applied. If the pressure tip injectors 328 were allowed to contact the microchip 7 before engagement of the tube-in-tube assembly 314, significantly more force would be required to lower arm 318 in order to compress the o-ring seals of the pressure tip injectors during engagement. If there happened to be any interference between any of the pressure tip injectors 328 and the anode ports 5 or between the tube-in-tube assembly 314 and the inlet ports 9 on the microchip 7, due to a manufacturing defect or some other problem, the pressure tip injectors 328 tips, the tube-in-tube assembly 314 or the microchip substrate 7 might sustain damage due to the higher forces involved. In addition, allowing independent motion of the pressure tips compensates for manufacturing tolerances of the various parts that make up the system. In a preferred embodiment the o-rings 508 of the pressure tip injectors 328 contact the anode ports 5 of the microchip substrate 7 after the tube-in-tube assembly 314 has engaged the inlet ports 9 of the microchip 7, as this results in less likelihood of damage.

Once the microchip is in place, the tube-in-tube assembly 314 has engaged the inlet ports 9 of the microchip substrate 7 and the pressure tip injectors 328 have engaged the anode ports 5, the pressure valves 400 (FIG. 19) and the vacuum valves 402 (FIG. 20) are activated. During operation, pressure valves 400 connected at one end by pressure supply tubing 310 to containers of solution 308 and connected by pressure tubing 310 at the other end to the upper compartments of the manifold 302 are activated Pressurized solutions such as water or wash are selected and allowed to flow by proper pressure valve 400 actuation.

Each group of pressure supply tubes is addressable by actuating the proper pressure valve 400. The upper arrows in FIG. 18(*a*) indicate the direction of flow of the pressurized solution being introduced into each side opening 626 of the upper compartment 410 of the upper chamber 304 of the manifold 302 through the pressure supply tubes 310 connected to the pressure valves 400 and containers of solution 308. The six pressure supply tubes are separated into three groups of two, each group of two connected to a separate pressure fluid control valve 400. The pressurized solutions in the compartment 410 flow within the pressure tubes 606 of the tube-in-tube assembly 314 from the upper compartment 410 to the inlet ports 9 on the microchip substrate 7 in order that the inlet ports 9 of the substrate 7 may be washed. The pressure applied to the solutions flowing through the manifold 302 is approximately a few PSI. Different solutions may be used in any combination for each upper compartment. Though only one upper 410 and lower 416 compartment are pictured here, any number of compartments may be present forming the upper 304 and lower 306 chambers of the manifold 302.

At the same time, the vacuum valves 402 (FIG. 20) are activated so that solution present within each of the inlet ports 9 of the microchip substrate is vacuumed out of the inlet ports by the individual vacuum tubes 608 of the tube-in-tube assembly 314 into the lower compartment 416 of the manifold 302 and into the vacuum supply tubes 312 connected to the side openings 628 of the lower chamber 306. The vacuum may range from approximately 5–29 inches of mercury.

Next, solution is injected into the capillary microchannels 3 of the microchip substrate 7 through the anode ports 5. It is desirable that injected solution is pre-filtered as matrix is, or filtered as it is routed to the anode ports 5, as the small dimensions of the capillary microchannels 3 cause the microchannels to be prone to clogging. The stream selector valve 334 (FIG. 16) is activated such that the selected fluid begins to flow within the tubing from the reservoir of solution 332 or containers 309 to the T apparatus 336 where the tubing 330, and the solution contained within, split in both directions. The tubing 330 enters each of the pressure tip injectors 328 arranged within the openings of the pressure injector block 326 and sealed to the anode ports 5 of the microchip substrate 7 with O-rings 508 (FIGS. 21 and 22). The solution present within the tubing 330 is injected from the pressure tip injectors into the anode ports 5 under high pressure to the microchannels. High pressure, in the range of approximately 250 PSI, is desired due to the resistance offered by the small dimensions of the capillary microchannels 3. However, even higher pressures may be used if the O-rings 508 form a reliable seal to the anodes 5.

If the intent is to store the microchip substrate rather than reuse immediately, the microchannels 3 are washed with high pressure wash solutions injected into the anode ports 5 through the use of the pressure tip injectors 328. High pressure solutions introduced into the channels 3 through the anode ports 5 pump matrix and solution out of the channels into the inlet ports 9 where they are vacuumed by the vacuum tubes 608 surrounding the pressure tubes 606 into the lower compartment 416 (FIG. 20) and/or compartments 412 or 414 of the chamber 306 (FIG. 16). Matrix and solution flow out of the lower compartment 416 through the vacuum supply tubes 312 to the waste bottle 420 (FIG. 20). Although the anode ports 5 are not vacuumed, they are washed as replacement matrix or high pressure solutions are pumped in.

After the matrix has been sufficiently cleared, lower pressure fluid is selected by the stream selector valve 334 and is flowed through the capillary channels 61 for the desired time. Air or nitrogen may then be injected into the microchannels to prepare the microchip substrate 7 for storage. When the substrate is ready to be used, regeneration fluids followed by matrix are pumped into the microchannels through the anode ports 5.

If the microchip substrate is being reused rather than stored, the microchannels of the microchip substrate need not be cleaned with pressurized wash or solution, unless desired. The old matrix is pumped out as fresh matrix is pumped in. The old matrix is suctioned out by the vacuum tubes 608 of the tube-in-tube assembly 314 present in the inlet ports 9 of the microchip substrate 7. Once the microchannels have been pumped with a sufficient amount of new matrix, the selector valve 334 is switched to the off position. The inlet ports are then washed and suctioned with the tube-in-tube assembly 314. Next, the manifold pressure tube cleaning fluids are turned off and when the inlet ports 9 are suctioned empty, the vacuum is switched off so that buffer or sample may be added. The arm 318 is raised and microchip substrate 7 may be removed. The entire process can be performed manually or is easily automated by utilizing the appropriate valves and control hardware/software.

In another embodiment of the invention, the tube-in-tube assembly comprises only one pressure tube 606 surrounded by one vacuum tube 608 rather than a plurality. This single tube-in-tube device is mounted on a robotic stage that quickly moves it between inlet ports. Alternatively, a tube-in-tube assembly that has a group of pressure tubes each surrounded by a vacuum tube is provided. The group of pressure tubes may be moved between groups of inlet ports on the microchip substrate 7.

In an alternative embodiment of the invention, the tube-in-tube assembly 314 may be inserted within the anode openings 5 of the microchip 7 for use as described above. Conversely, the pressure injector tips 328 may be inserted within the inlet ports 9 of the microchip 7 for use as described above. Alternatively, the positioning of vacuum tubes and pressure tubes of the tube-in-tube assembly may be reversed. The positioning of the vacuum supply tubes are pressure supply tubes may also be reversed.

In this document, when reference is made to a "pipettor", the term should be understood to include, but not be limited to, a single pipettor, a multichannel pipettor, a capillary pipettor or a microfluidic device, a piezoelectric device or other means to move fluids. When reference is made to a "plate", the term should be understood to include, but not be limited to, a microtiter plate, a tube, a microarray device, a reservoir or device that can store or output samples, such as a microfluidic device. Although the main example above relates to electrophoresis, similar apparatus could be used for electrochromatography, gas chromatography, and liquid chromatography. Also, filling of the microchannels is not limited to micropipettor devices. For example, tiny capillaries could be used. Such non-pipettor devices need not match the hole spacing in the microchip. Such devices may be moved from one inlet port to the next.

What is claimed is:

1. An apparatus for filling and cleaning an analytical substrate of the type having microchannels, said microchannels having a plurality of inlet ports and a plurality of anode ports separated by a length of the microchannel, comprising:

an arm mounted on the apparatus such that the arm may be raised and lowered;

a tube-in-tube assembly having a plurality of tube assembly pressure tubes and a plurality of tube assembly vacuum tubes paired one inside the other;

a manifold mounted on said arm upon which said tube-in-tube assembly is mounted, said tube-in-tube assembly allowing a pressurized liquid to be distributed by said manifold into said pressure tubes and a vacuum source to be distributed by said manifold to said vacuum tubes; and an injector mounted on said arm and spaced from said tube-in-tube assembly by a distance substantially corresponding to the length of the microchannel, wherein when said arm is lowered, ends of said pressurized tubes seal over inlet ports on said substrate and said injector also seals over an anode port on said substrate.

2. The apparatus of claim 1 wherein the manifold has a first chamber for providing pressurized solutions from a pressurized container to said substrate and a second chamber for vacuuming solution from said substrate with a vacuum source.

3. The apparatus of claim 2 wherein said first chamber of said manifold is above the second chamber of said manifold.

4. The apparatus of claim 3 wherein said first chamber of the manifold includes a plurality of first compartments.

5. The apparatus of claim 2 wherein said plurality of pressure tubes of said tube-in-tube assembly is inserted into a plurality of openings on a lower surface of said first chamber of the manifold.

6. The apparatus of claim 3 wherein said second chamber of the manifold comprises a plurality of second compartments.

7. The apparatus of claim 6 wherein said second chamber of the manifold comprises three second compartments.

8. The apparatus of claim 6 wherein said second compartments have at least one opening.

9. The apparatus of claim 8 further comprising at least one vacuum supply tube connected to a vacuum source and inserted into the openings of said second compartments.

10. The apparatus of claim 3 wherein said plurality of pressure tubes of said tube-in-tube assembly are inserted into said plurality of vacuum tubes of said tube-in-tube assembly.

11. An apparatus for filling and cleaning an analytical substrate of the type having microchannels including a plurality of input ports and a plurality of anode ports separated by a length of said microchannels comprising:

a container storing a liquid solution;

a vacuum source;

an arm that may be raised and lowered over a substrate having microchannels and microchannel openings;

a manifold mounted on said arm joined to said container and said vacuum source such that said manifold could distribute liquid solution and vacuum from said container and vacuum source, respectively;

a tube-in-tube assembly extending from said manifold and comprising a plurality of tube assembly pressure tubes and a plurality of tube assembly vacuum tubes paired one inside the other, wherein lowering of said arm allows tubes in said tube-in-tube assembly to seal over input ports on said substrate allowing solution distribution from said container to inlet ports of said substrate and also allowing solution removal by suction through said tube-in-tube assembly from said substrate inlet ports; and an injector mounted on said arm and spaced from said tube-in-tube assembly by a distance substantially corresponding to the length of the microchannel, wherein lowering said arm brings the injector in pressure communication with the anode ports, wherein said tube-in-tube assembly and said injector allow sealing of both input ports and anode ports when said arm is lowered.

12. The apparatus of claim 11 further comprising a platform for holding said substrate.

13. The apparatus of claim 11 further comprising a means for positioning said manifold.

14. The apparatus of claim 13 further comprising a sensor assembly indicating when the arm has been lowered.

15. The apparatus of claim 11 wherein said manifold has a first chamber for providing pressurized solutions from said container to said substrate and a second chamber for vacuuming solution from said substrate with said vacuum source.

16. The apparatus of claim 15 further comprising first and second compartments within respective first and second chambers and a separate control associated with said first and second compartments.

17. The apparatus of claim 11 further including a means for automated operation of said apparatus.

18. An apparatus for filling and cleaning an analytical substrate of the type having microchannels including a plurality of microchannel inlet ports and a plurality of microchannel anode ports, said inlet ports and anode ports separated by a length of said microchannel comprising:

a container;

a vacuum source;

an arm that may be raised or lowered over the substrate;

a manifold mounted on the arm in pressure tight fluid communication with said container and vacuum source, wherein solution is provided from the container to said substrate and solution is removed from said substrate with said vacuum source, said manifold having an upper chamber having a plurality of first compartments having a first plurality of openings on a lower surface of each of said plurality of first compartments, and a lower chamber having a plurality of second compartments having a second plurality of openings on a lower surface of said plurality of second compartments, wherein said second plurality of openings on said lower surface of said lower chamber are larger than said first plurality of openings on said lower surface of said upper chamber first compartments, said first plurality of openings being in vertical alignment with said second plurality of openings;

a plurality of pressure tubes inserted into first openings of said upper chamber first compartments and in fluid communication with said container through said manifold;

a plurality of vacuum tubes inserted into said second openings of said lower chamber second compartments and in vacuum communication with said vacuum source through said manifold, wherein said pressure tubes extend through said vacuum tubes;

an assembly for fluidic and pressure communication with said first and second compartments of said upper and lower chambers of said manifold and inlet ports of said substrate wherein said assembly allows for simultaneous distribution and suction of fluid to and from said substrate and said upper and lower chamber of said manifold; and an injector mounted on said arm and spaced from said tube-in-tube assembly by a distance substantially corresponding to the length of the microchannel such that when said arm is lowered the injector is in pressure communication with the substrate for injecting a liquid media into the microchannels through the anode ports of said substrate wherein each of said plurality of microchannels is formed on a surface of said substrate and has an inlet port.

* * * * *